(12) United States Patent
Bennett et al.

(10) Patent No.: US 9,827,412 B2
(45) Date of Patent: *Nov. 28, 2017

(54) SYSTEMS AND METHODS FOR TREATING SHOULDER PAIN RELATED TO SUBACROMIAL IMPINGEMENT SYNDROME

(71) Applicant: SPR Therapeutics, LLC, Cleveland, OH (US)

(72) Inventors: Maria E. Bennett, Beachwood, OH (US); Joseph W. Boggs, II, Chapel Hill, NC (US); John Chae, Strongsville, OH (US)

(73) Assignee: SPR Therapeutics, LLC, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/202,256

(22) Filed: Jul. 5, 2016

(65) Prior Publication Data

US 2017/0056645 A1    Mar. 2, 2017

Related U.S. Application Data

(63) Continuation of application No. 14/536,951, filed on Nov. 10, 2014, now Pat. No. 9,381,343, which is a continuation of application No. 13/991,033, filed as application No. PCT/US2011/063304 on Dec. 5, 2011, now Pat. No. 8,886,337.

(60) Provisional application No. 61/419,537, filed on Dec. 3, 2010, provisional application No. 61/540,934, filed on Sep. 29, 2011.

(51) Int. Cl.
| | | |
|---|---|---|
| *A61N 1/00* | (2006.01) |
| *A61N 1/05* | (2006.01) |
| *A61N 1/36* | (2006.01) |
| *A61N 1/02* | (2006.01) |
| *A61N 1/08* | (2006.01) |
| *A61N 1/04* | (2006.01) |

(52) U.S. Cl.
CPC ........ *A61N 1/0504* (2013.01); *A61N 1/025* (2013.01); *A61N 1/0502* (2013.01); *A61N 1/0551* (2013.01); *A61N 1/08* (2013.01); *A61N 1/36071* (2013.01); *A61N 1/0456* (2013.01)

(58) Field of Classification Search
USPC ........................................... 607/116
See application file for complete search history.

(56) References Cited

U.S. PATENT DOCUMENTS

| | | | |
|---|---|---|---|
| 6,461,357 B1 | 10/2002 | Sharkey et al. |
| 2002/0068930 A1 | 6/2002 | Tasto et al. |
| 2006/0069415 A1* | 3/2006 | Cameron ........... A61N 1/36185 607/45 |

* cited by examiner

*Primary Examiner* — Nicole F Johnson
(74) *Attorney, Agent, or Firm* — McDonald Hopkins LLC

(57) ABSTRACT

Systems and methods are provided for treating chronic pain occurring secondarily to subacromial impingement syndrome in a human body. A system is provided to deliver percutaneous electrical stimulation through at least one electrode to neurological motor points of the posterior and middle deltoid muscles to mediate such pain. One-time, continued and/or periodic dosing of treatment methods according to the present invention may result in a change to central nervous system maladaptive neuroplasticity.

10 Claims, 16 Drawing Sheets

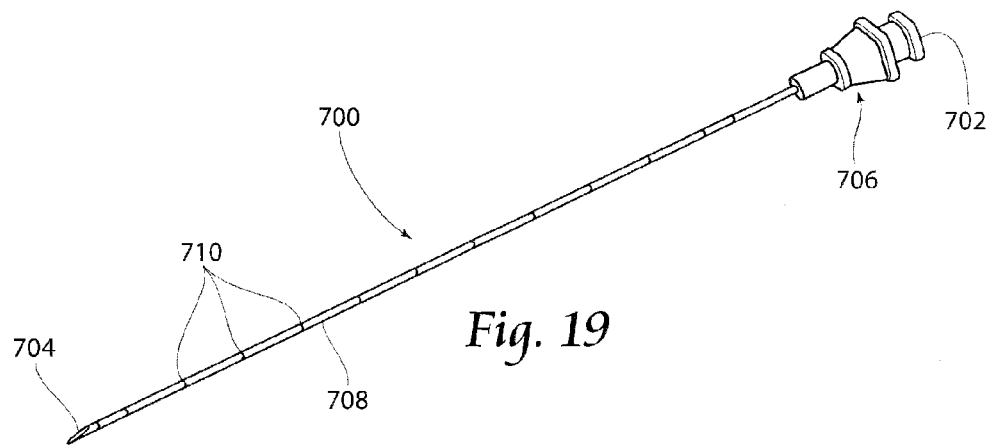
Fig. 19
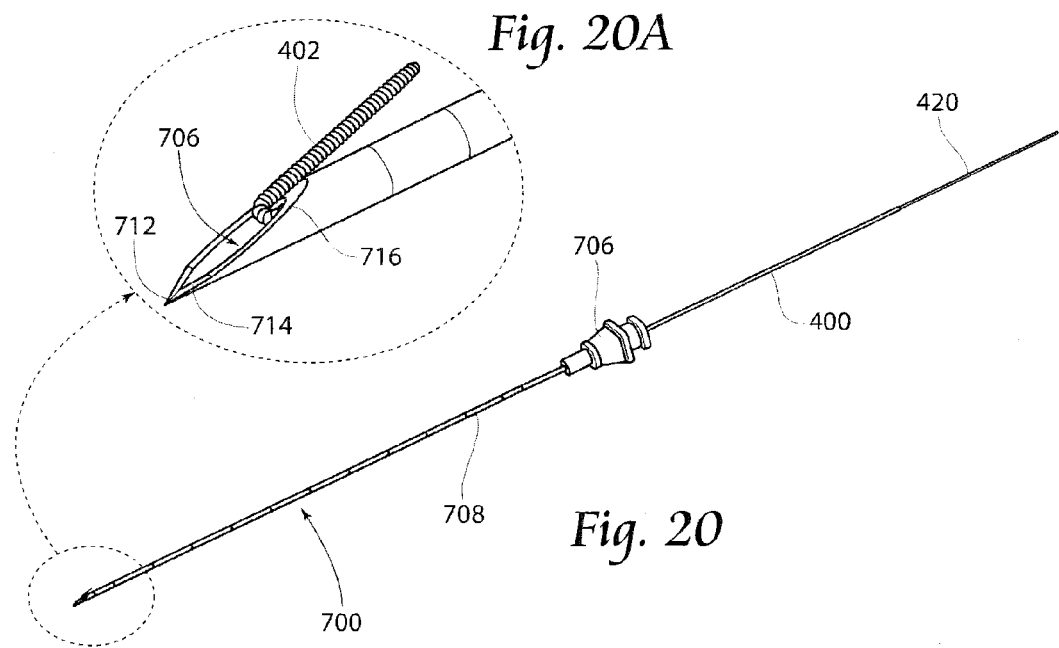
Fig. 20A
Fig. 20

SYSTEMS AND METHODS FOR TREATING SHOULDER PAIN RELATED TO SUBACROMIAL IMPINGEMENT SYNDROME

RELATED APPLICATIONS

This application is a continuation of U.S. application Ser. No. 14/536,951, filed on Nov. 10, 2014, entitled Systems and Methods For Treating Shoulder Pain Related to Subacromial Impingement Syndrome," which is a continuation of U.S. application Ser. No. 13/991,033 filed on 21 Oct. 2013, entitled "Systems and Methods For Treating Shoulder Pain Related to Subacromial Impingement Syndrome," now U.S. Pat. No. 8,886,337, which is a 371 National Phase Application of International Application No. PCT/US2011/063304, filed on 5 Dec. 2011, entitled "Systems and Methods For Treating Shoulder Pain Related to Subacromial Impingement Syndrome," which claims the benefit of U.S. Provisional Patent Application No. 61/419,537, filed 3 Dec. 2010, and entitled "Systems and Methods for Treatment of Pain caused by Subacromial Impingement," and also claims the benefit of U.S. Provisional Patent Application No. 61/540,934, filed 29 Sep. 2011, and entitled "Systems and Methods for Treating Shoulder Pain Related to Subacromial Impingement Syndrome," which are all incorporated by reference herein in their entirety.

BACKGROUND OF THE INVENTION

Shoulder pain is a common medical problem with social and economic consequences: shoulder problems account for more than 12 million visits to physicians annually in the US. A systematic review of literature regarding studies on shoulder pain found that point prevalence ranges from about seven to about 27 percent of the general population of adults less than 70 years of age, with one year prevalence being up to about 47 percent. The wide range is attributed to inconsistent ways in which the shoulder area is defined. Annual incidence rates vary between 0.9 and 2.5% of the general population depending on age. Subacromial impingement syndrome (SIS) is the most common cause of shoulder pain, accounting for 48% of incident cases. Anatomically, SIS refers to the supraspinatus tendon impinging on the undersurface of the anterior acromion as the arm is raised overhead. Typically, pain is generated with elevation of the arm above the head though it can occur with rest. Multiple pathologies, such as subacromial bursitis, rotator cuff tendinopathy, partial rotator cuff tears, and even small tears can coexist to create SIS.

Shoulder pain greatly affects quality of life (QOL). One study found that 84% of subjects with shoulder pain slept less well, 85% had problems moving their arm or hand, and 45% were more irritable. The socioeconomic burden of shoulder pain is also substantial. Shoulder disability can impair one's ability to work and perform household tasks, and results in, on average, 12% lost productive time from work in the US.

Shoulder pain secondary to SIS is not adequately addressed by present therapies. The pain treatment continuum, especially during the acute and subacute phases, begins with conservative treatments such as non-steroidal anti-inflammatory drugs (NSAIDs). Though minimally invasive, these medications are ineffective in the long term for up to half of patients, and commonly have systemic side effects such as headache, skin rash, dizziness, and gastrointestinal symptoms. Other conservative therapies include physical therapy and injections. When ineffective, and as the pain syndrome enters the chronic phase, these conservative therapies are followed by opioid medications or surgical management.

Current treatment options for chronic pain also include physical therapies, oral analgesic medications, local injection techniques, surgery, and neurostimulation. The present treatment options demonstrate marginal pain relief and have undesired side effects. Present neurostimulation methods have clinical and technical difficulties preventing them from becoming the standard of care and more widely adopted. Surface neurostimulation systems are difficult to implement due to the discomfort of stimulation felt on the skin and the need for skilled personnel to place electrodes properly on a daily basis. Implantable neurostimulation systems (e.g., spinal cord stimulation) require placement of the device in the spinal canal (e.g. in the epidural space), which has the potential for nerve damage, unwanted device movement within the spinal column, and repeat clinic visits for re-adjustment. Historically, peripheral nerve stimulators for pain have not achieved widespread clinical success, due to the need to dissect or expose nerves in an open surgical procedure and place leads directly in contact with these target nerves.

Thus, currently available therapies are unsatisfactory in treating shoulder pain. Forty to fifty percent (40-50%) of patients who visit a general practitioner continue to report shoulder pain after 12 months of conservative therapy. Currently there is no commonly accepted standard of care for shoulder pain. Rest (avoiding offending movements such as elevation of the arm over the head), non-steroidal anti-inflammatory drugs, physical therapy, and corticosteroid injections are most commonly used for treating shoulder pain secondary to SIS, regardless of the exact pathology. When these fail, surgery is considered, but surgical pain management due to SIS is no more effective than conservative therapies, leaving 40-50% of patients without an effective treatment for their chronic pain.

Accordingly, the art of shoulder pain therapy would benefit from safe and effective short- and long-term peripheral nerve stimulation (PNS) therapies for patients with moderate to severe acute, sub-acute and even chronic (>6 month) shoulder pain secondary or related to SIS.

SUMMARY OF THE INVENTION

Embodiments according to the present invention are adapted to provide safe and effective short- and long-term peripheral nerve stimulation (PNS) therapies for patients with moderate to severe acute, sub-acute and even chronic (>6 month) shoulder pain secondary or related to SIS.

BRIEF DESCRIPTION OF THE DRAWINGS

FIG. 19 is a perspective view of an introducer according to the present invention.

FIG. 20 is a perspective view of the introducer of FIG. 19 loaded with the lead of FIG. 18.

FIG. 20A is a partial perspective view of an embodiment of an introducer needle according to the present invention.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
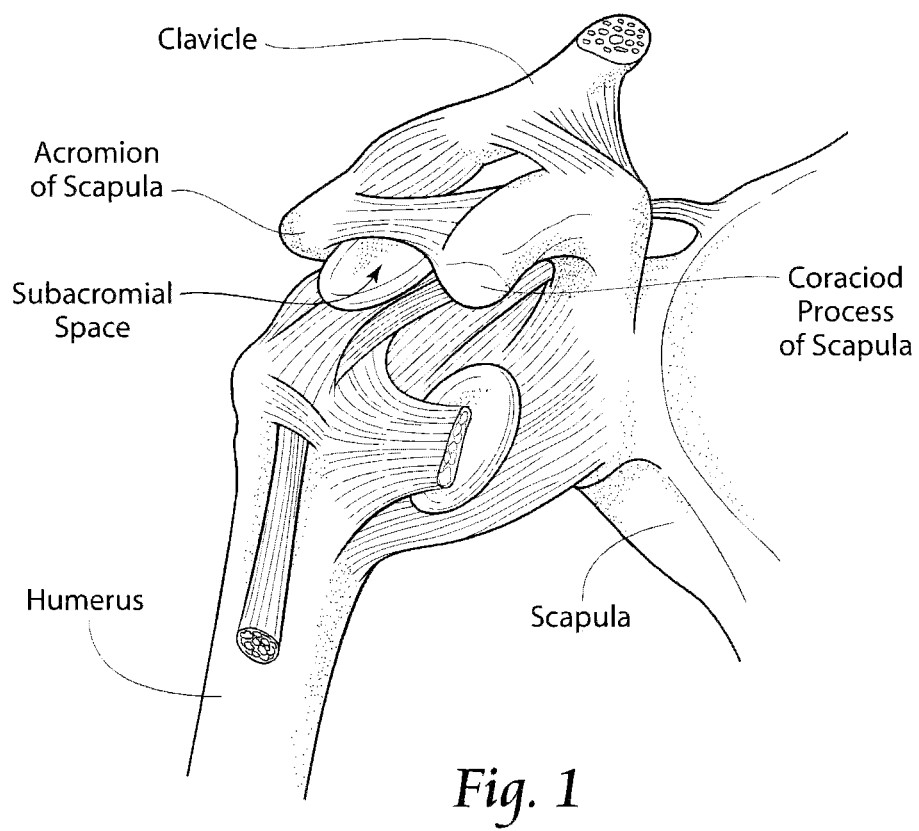
FIG. 1 depicts an anatomical view of a human shoulder joint.
Figure 2:
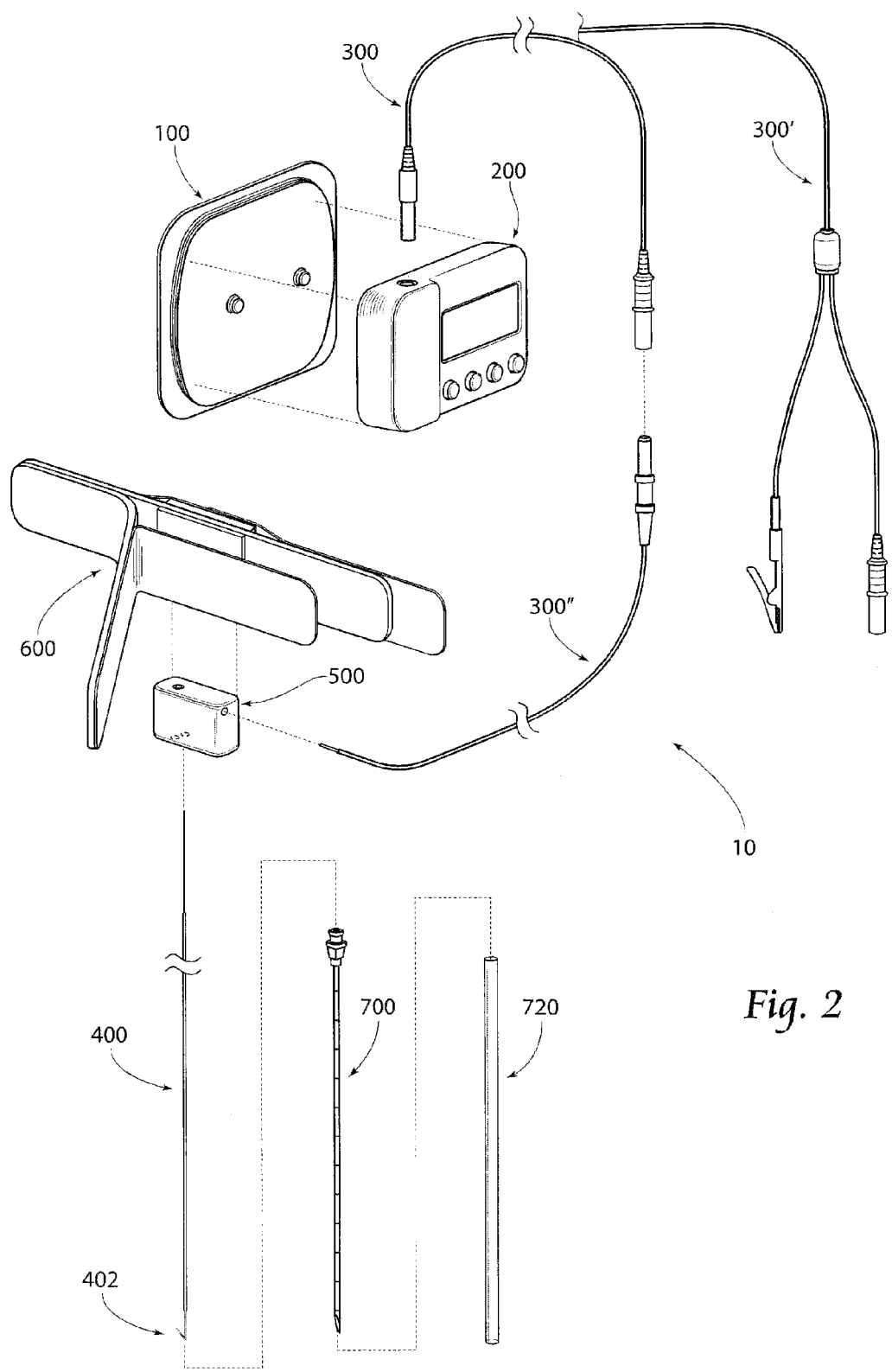
FIG. 2 is a perspective assembly view of an embodiment of an electrical stimulation system according to the present invention.

Turning now to the figures, FIG. 2 depicts components of one or more electrical stimulation systems according to the present invention. Preferably, an electrical stimulation system 10 according to the present invention includes a mounting patch assembly 100, an electrical stimulator 200, one or more electrical cables 300, and one or more stimulating electrodes 402 that may be carried on a percutaneous electrical lead 400. Embodiments according to the present invention also include electrical connectors 500 and connector mounting structure 600.

As used herein, the term "percutaneous" is to be understood to describe an electrical stimulation that is provided to animal tissue, where the source of the stimulation (e.g. device/tissue interface) is an electrode that is positioned subepidermally. Percutaneous stimulation may be provided a number of ways, such as by an electrical conductor (e.g., wire) configured to be utilized while protruding through the epidermis of the animal. Alternatively, percutaneous stimulation may be provided by an implanted electrode that is wirelessly controlled and/or powered by a control unit positioned outside of the animal body.

The term "percutaneous" may be contrasted with the term "transcutaneous," which is conventionally understood to involve the application of electrical stimulation to an animal body through electrodes (e.g. surface electrodes or EKG electrodes), which are in electrical contact with the epidermis of the animal. While generally preferred embodiments according to the present invention include systems and methods of percutaneous stimulation, it is to be understood that various components of systems according to the present invention may be utilized in other methods of stimulation, such as transcutaneous stimulation, and even outside the field of electrical stimulation altogether.

While a percutaneous system is herein described, it is to be understood that applicable treatments may be provided initially by such percutaneous system and, if desirable, treatments may be continued through the use of an implantable electrical stimulator, where such stimulator and stimulation is contained entirely under the epidermis of the animal.

Patch Assembly

FIG. 2 provides an assembly view of a preferred patch assembly 100 according to the present invention. The preferred patch assembly 100 is comprised of several layers, including an adhesive layer 102, an electrode layer 104, a reinforcement layer 106, and a cover layer 108. All of the layers 102, 104, 106, 108 are preferably substantially the same length and width, so as to form a generally uniform stack of layers when assembled. The adhesive layer 102 is preferably formed from a desired thickness (e.g. such as about 20 to about 30 mils, with about 25 mils being most preferred) of electrically conductive hydrogel. The electrode layer 104 is a conductive material, preferably formed from a carbon or carbon/silver film of a desired thickness, such as about 2.35 mils. The reinforcement layer 106 is preferably formed from a polyethylene film coated on one side 106a with a contact pressure sensitive acrylic adhesive. The reinforcement layer 106 and adhesive is preferably provided at a desired thickness, such as about five to about six mils. The cover layer 108 is preferably a durable tape material, which preferably has a matte, or non-reflective finish. An example of desirable tape material is a polyester fabric tape of a desired thickness, such as about 13 mils. The overall length 101 and width 103 of a preferred patch assembly 100 according to the present invention are about 2.5 inches by about 2.5 inches, respectively, and more preferably about 2.625 inches by about 2.5 inches respectively. Provided as a protective cover to the adhesive layer 102 may be an adhesive neutral liner 105, such as a silicone coated polyester film of a desired thickness, such as about four mils.

Also preferably provided on the patch assembly 100 is a power source, such as a battery assembly 110. The battery assembly 110 may be positioned and held securely substantially between two of the layers already described, such as between the conductive layer 104 and the reinforcement layer 106. The battery assembly 110 is preferably formed from one or more conductor assemblies 112,114 and a battery 116. The battery 116 has a preferred capacity and provides a desired voltage, such as about fourteen milliamp-hours and about two to about three volts, respectively, and is provided with a first terminal 118 and a second terminal 120. However, a stimulator 200 according to the present invention may function with a battery providing as little as 6.8 mA-hr down to a voltage of about 2.4 volts. A preferred battery is a flexible lithium polymer primary cell battery, such as an SF-2529-14BC battery available from Solicore, Inc., of Lakeland, Fla. A preferred battery 116 preferably has a size of about 25 millimeters by about 30 millimeters by about 0.5 millimeters, with a size of 26 mm×29 mm×0.45 mm being most preferred.

A first conductor assembly 112 is formed from a snap member 122 coupled to a copper foil conductor 124. The copper foil conductor 124 is preferably substantially L-shaped having a substantially rectilinear body portion 124a formed along a longitudinal axis 125 and a leg portion 126 extending preferably co-planar from the body portion 124, preferably orthogonal to the longitudinal axis 125. The body portion 124 may be folded onto itself to form a dual layer portion 124b with enhanced durability and support for the snap member 122. A preferred snap member 122 is preferably a male conductive snap assembly including a shank member 122a and a receiver member 122b. The shank member 122a is at least partially received into the receiver member 122b and secured thereto. Preferred receiver members 122b are formed from nickel plated brass configured to mate with conventional 4 mm medical industry standard parallel spring female snaps. Preferred shank members 122a are silver or silver chloride coated molded plastic substrate. The shank member 122a is positioned through a snap aperture 130 formed through the copper foil conductor assembly 124, such as through the dual layer portion 124b. The snap aperture 130 may be formed prior to insertion of the shank member 122a, or may be formed by or simultaneously with the insertion of the shank member 122a through the foil conductor 124.

A second conductor assembly 114 is also formed from a snap member 132 coupled to a copper foil conductor 134. The copper foil conductor 134 is preferably substantially U-shaped with a first leg 136 coupled to a second leg 138 through a base portion 140. The first leg 136 is formed in a preferably substantially rectilinear formation having a length 136a disposed along a first leg axis 137, and a width 136b measured perpendicular to the first leg axis 137. The second leg 138 is formed in a preferably substantially rectilinear formation having a length 138a disposed along a second leg axis 139, and a width 138b measured perpendicular to the second leg axis 139. The second leg axis 139 is preferably disposed at least substantially parallel to the first leg axis 137. The first leg length 136a is preferably substantially similar or equal to or less than the second leg length 138a. The first leg 136 may be folded onto itself to form a dual layer portion 136c with enhanced durability and support for the snap member 132. The first leg 136 and the second leg 138 are preferably disposed at least substantially coplanar with each other and electrically coupled by the base portion 140, spacing the first leg 136 from the second leg 138 by a preferred insulative gap 142. Extending from the second leg 138 into the insulative gap 142, preferably perpendicular to the second leg axis 139, is a conductor tab 144, configured to be folded over the battery 116 and soldered to the second battery terminal 120. A preferred snap member 132 is preferably a male conductive snap assembly including a shank member 132a and a receiver member 132b. The shank member 132a is at least partially received into the receiver member 132b and secured thereto. Preferred receiver members 132b are formed from nickel plated brass configured to mate with conventional 4 mm medical industry standard parallel spring female snaps. Preferred shank members 132a are silver or silver chloride coated molded plastic substrate. The shank member 132a is positioned through a snap aperture 146 formed through the first leg 136, such as through the dual layer portion 136c. The snap aperture 146 may be formed prior to insertion of the shank member 132a, or may be formed by or simultaneously with the insertion of the shank member 132a through the foil conductor 134.

To assemble the battery assembly 110, the first conductor assembly 112 may be punched or otherwise cut or formed from a copper material and the snap member 122 coupled thereto. The first conductor assembly 112 is adhered to the battery 116, and the leg portion 126 is electrically coupled, such as by soldering, to the first battery terminal 118, thereby placing the snap 122 in electrical contact with the first terminal 118. The battery 116 is adhered to the second conductor assembly 114, preferably to the second leg 138, and the conductor tab 144 is electrically coupled, such as by soldering, to the second battery terminal 120, thereby placing the snap 132 in electrical contact with the second terminal 120. The second copper foil conductor 134 is placed in electrical communication with the conductive layer 104, such as by frictional contact or conductive adhesive, and the battery assembly 110 is preferably adhered to the conductive layer 104 and covered by the reinforcement layer 106 and the cover layer 108. Snap apertures 145 are cut, drilled, or otherwise formed through the reinforcement layer 106 and the cover layer 108 to align with the locations of the snap members 122,132 on the battery assembly 110.

Figure 3:
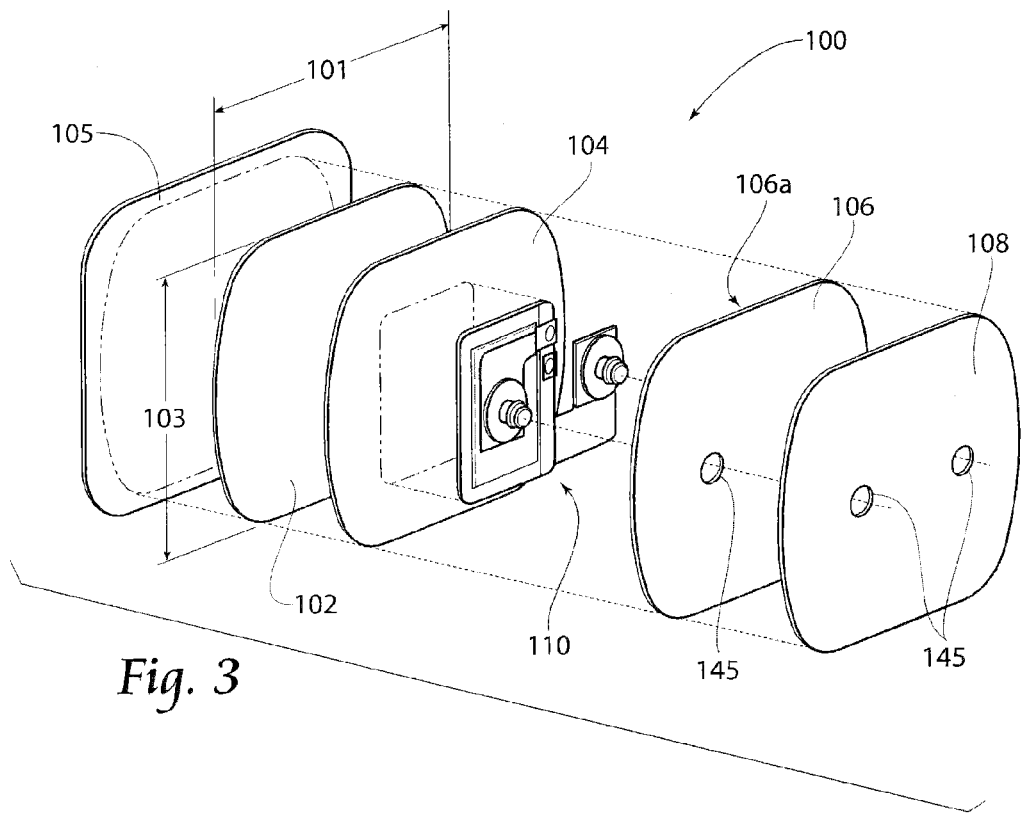
FIG. 3 is a perspective assembly view of an embodiment of a mounting patch according to the present invention.

FIG. 3B is a perspective view of an assembled battery assembly 110. Once assembled, the battery assembly 110 preferably offers the pair of snaps 122,132 spaced at a snap spacing 147 and provided substantially coplanar and lying in a line 149 that is at least substantially directionally perpendicular to the second leg axis 139. The source resistance of the battery 116 and its construction are such that overheating of the battery 116 is preferably not possible even with shorted terminals 118,120.

Electrical Stimulator

Figure 4A:
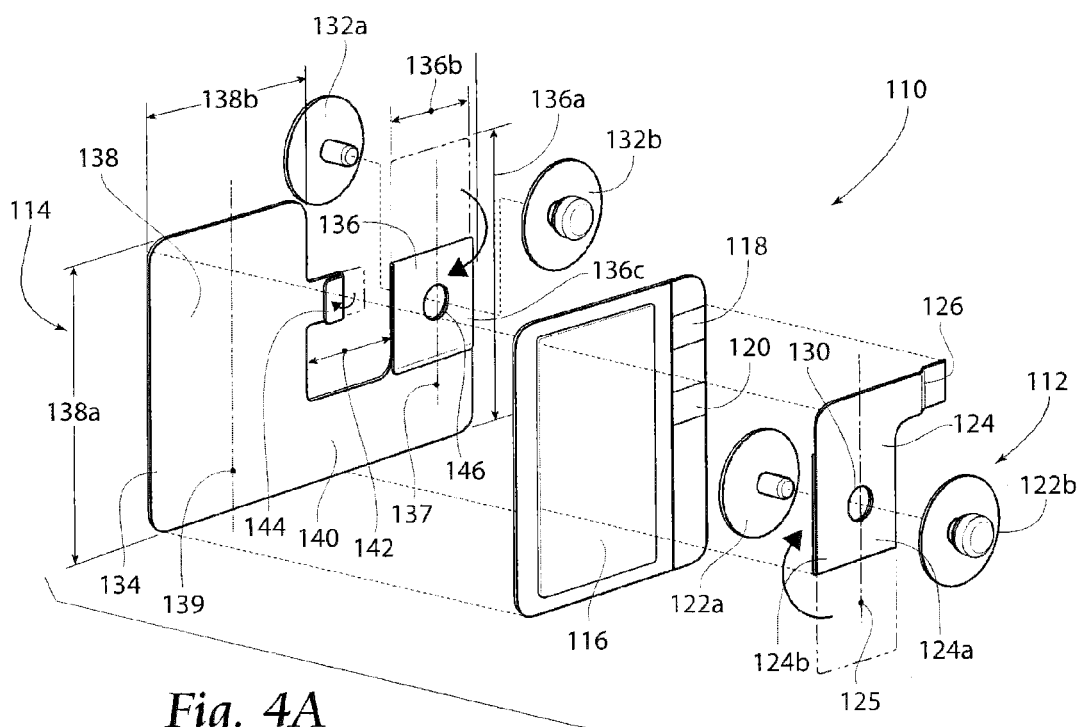
FIG. 4A is a perspective assembly view of an embodiment of a patch battery assembly according to the present invention.
Figure 4B:
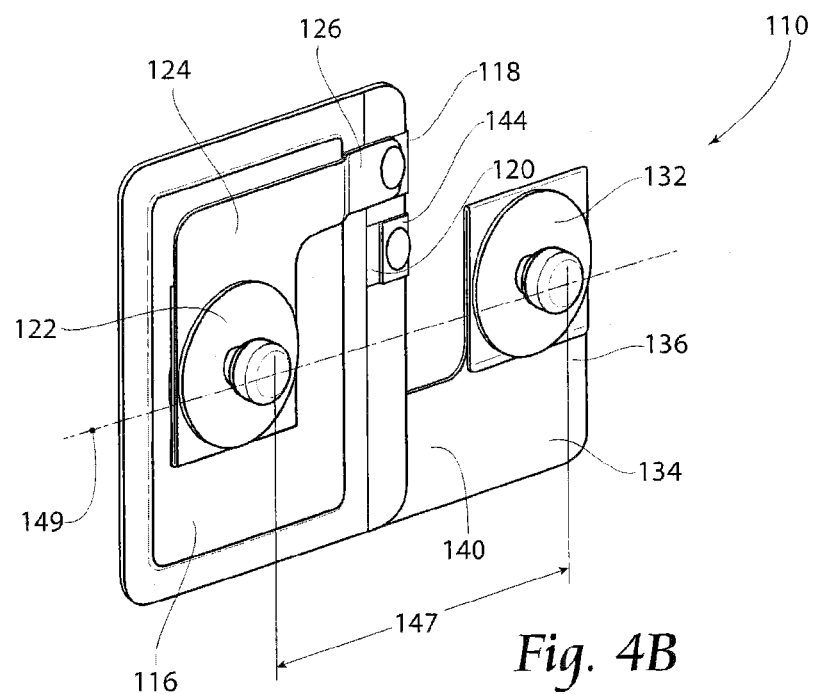
FIG. 4B is a perspective view of an assembled embodiment of a patch battery assembly according to the present invention.
Figure 5A:
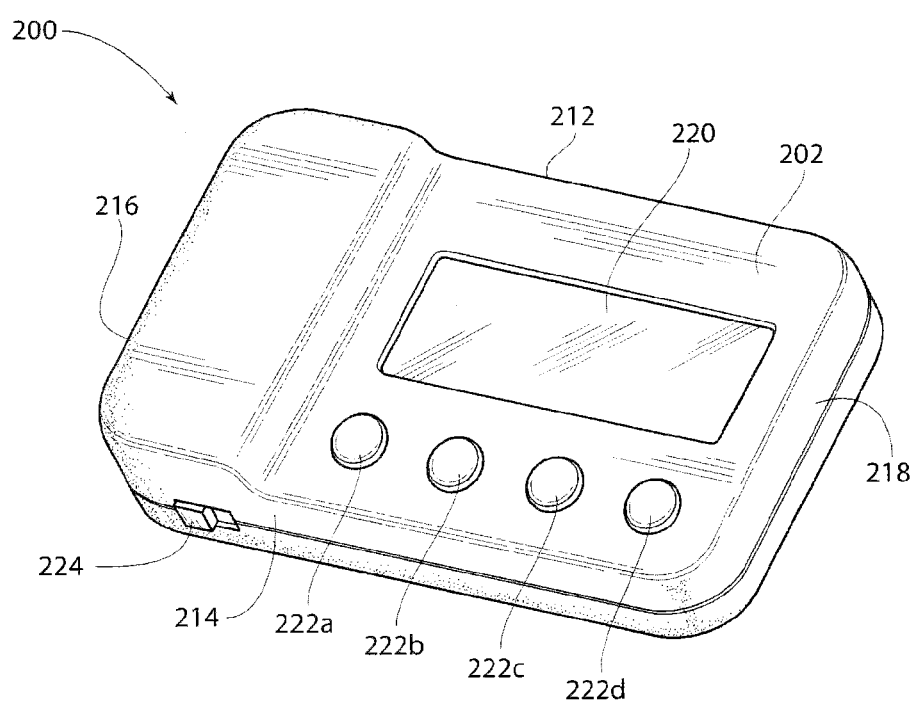
FIG. 5A is a perspective view of an embodiment of an electrical stimulator according to the present invention.
Figure 5B:
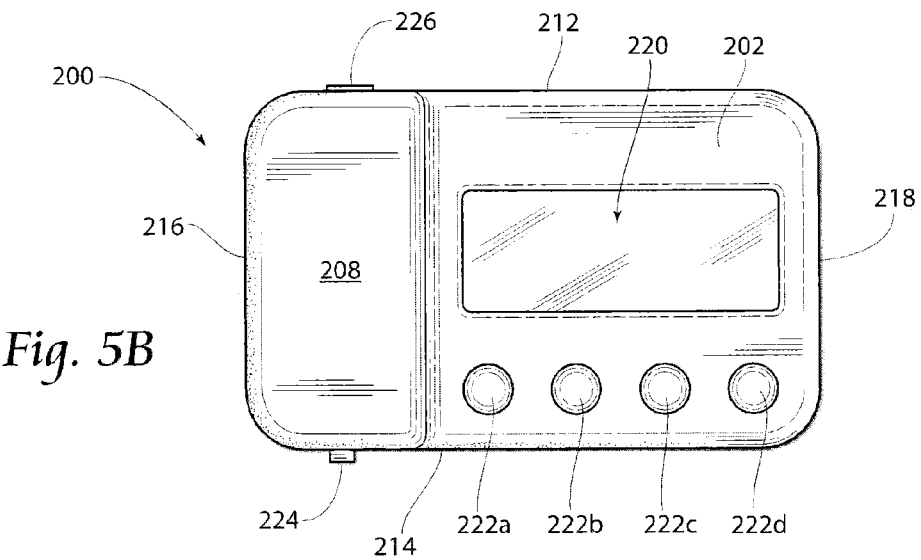
FIG. 5B is a front elevation view of the embodiment of FIG. 5A.
Figure 5C:
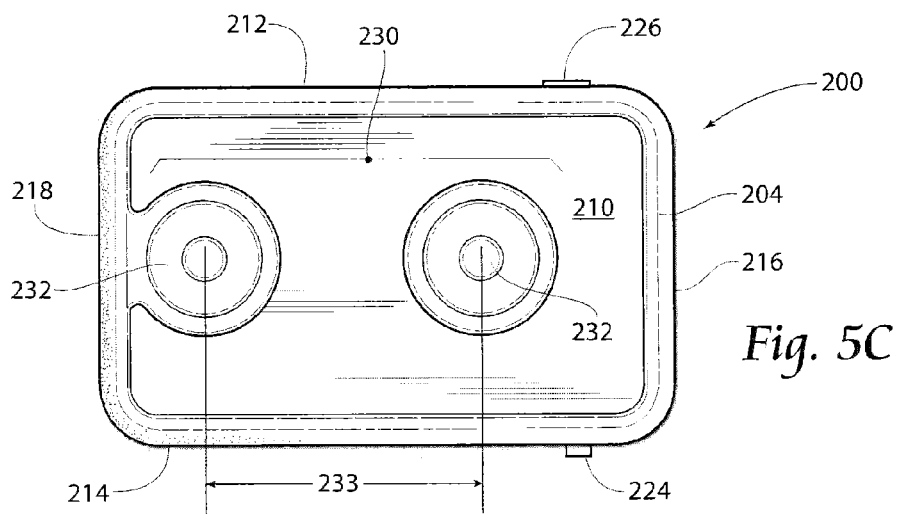
FIG. 5C is a rear elevation view of the embodiment of FIG. 5A.
Figure 5D:
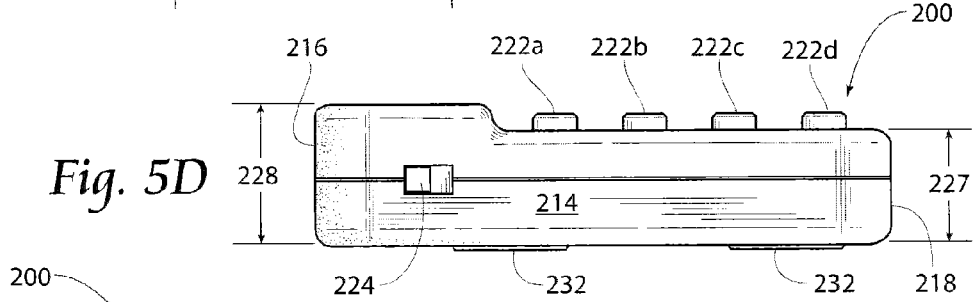
FIG. 5D is a bottom plan view of the embodiment of FIG. 5A.
Figure 5E:
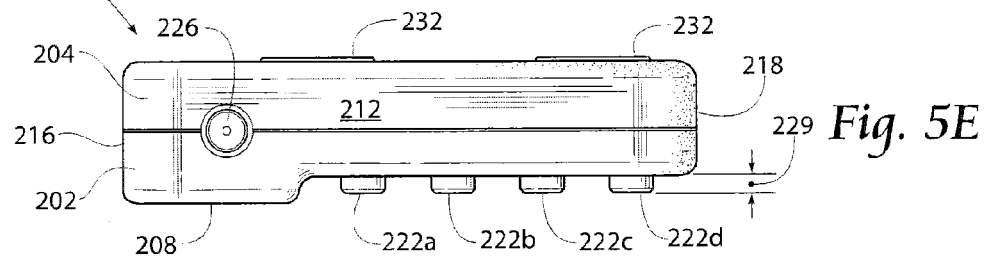
FIG. 5E is a top plan view of the embodiment of FIG. 5A.

Turning now to FIGS. 4A-5, an embodiment 200 of an electrical stimulator according to the present invention may be described. Generally, the stimulator 200 includes a housing 201 having a cover 202 and a base 204. The housing 201 generally forms a cavity 203 that is configured to at least partially contain a printed circuit board 206 on which electrical stimulation generation circuitry may be mounted. Generally, the housing 201 extends between and includes a front surface 208 and an opposed back surface 210, a top surface 212 and an opposed bottom surface 214, and a left surface 216 and an opposed right surface 218. The housing 201 may have a plurality of apertures or passageways 205 formed therethrough, allowing access to the cavity 203, either functionally or physically. Functional access may be provided to a user output interface, such as a display screen 220, or to a user input interface, such as one or more buttons or keys 222a,222b,222c,222d. Physical and/or functional access may be provided such as for one or more slide switches 224 or electrical connection, such as by way of a jack 226. The housing 210 preferably includes a housing thickness that may be measured between and include the front surface 208 and the back surface 210. The housing 201 may have a first thickness 227 and a second thickness 228, which is greater than the first thickness 227. If buttons 222 extend through the front surface 208 or the rear surface 210, the second thickness 228 is preferably greater than the sum of the first thickness 227 and any button thickness 229, measured perpendicular to the front surface 208 or rear surface 210, respectively. Such greater second thickness 228 assists in protecting from accidental engagement of the buttons 222 by bumping the stimulator 200 against something or from clothing interaction if the stimulator 200 is worn under a person's clothes.

Mounting structure 230 is preferably provided on or coupled to the back surface 210 of the housing 201. The mounting structure 230 preferably corresponds to mounting structure provided on the patch assembly 100, as described above, such as the snap members 122,132. Accordingly, the mounting structure 230 is preferably comprised of two female parallel spring snap members 232 spaced at a mating snap spacing 233, which is substantially the same as or equal to the snap spacing 147 provided on the patch assembly 100. As depicted, the mating snap spacing 233 may be provided off-center, that is, positioned closer to one of the left side 216 or right side 218 of the housing 201. Such arrangement may be preferable to enable centering of the stimulator 200 on the patch assembly 100, which is a preferred mounting arrangement. As mentioned above, a power source may be provided in a patch assembly 100, such as the battery 116. Electrical connection between the patch assembly 100 and the electrical stimulator circuit board 206 may be provided through the snap members 122,132,232. Within the housing 201, the female snap members 232 may be electrically coupled to the printed circuit board 206, e.g. through a plurality of wires 234. Alternatively, the stimulator 200 may be mounted to the patch assembly 100 through the snap members 122,132,232 for structural support or mounting only, and a power source, such as a lithium ion cell, could be provided within the housing 201. In such case, it would be unnecessary to electrically couple the female snap members 232 to the printed circuit board 206.

As mentioned, the housing 201 may provide functional access to a user output interface such as a liquid crystal display 220. The LCD 220 may be backlit or not backlit. Provided over the LCD may be a substantially planar, preferably transparent, cover or lens 236. A user input interface may also be provided by the one or more buttons 222 and/or slide switch 224. The one or more buttons 222 each correspond to a pushbutton switch 238, which may be mounted on the printed circuit board 206 and electrically coupled to a microcontroller. The slide switch 224 may also be mounted to the printed circuit board 206 and electrically coupled to the microcontroller. Usage of the user input interface will be more fully described below. The housing cover 202 is preferably held in mechanical engagement with the housing base 204 by a plurality of threaded fasteners 240.

Figure 6:
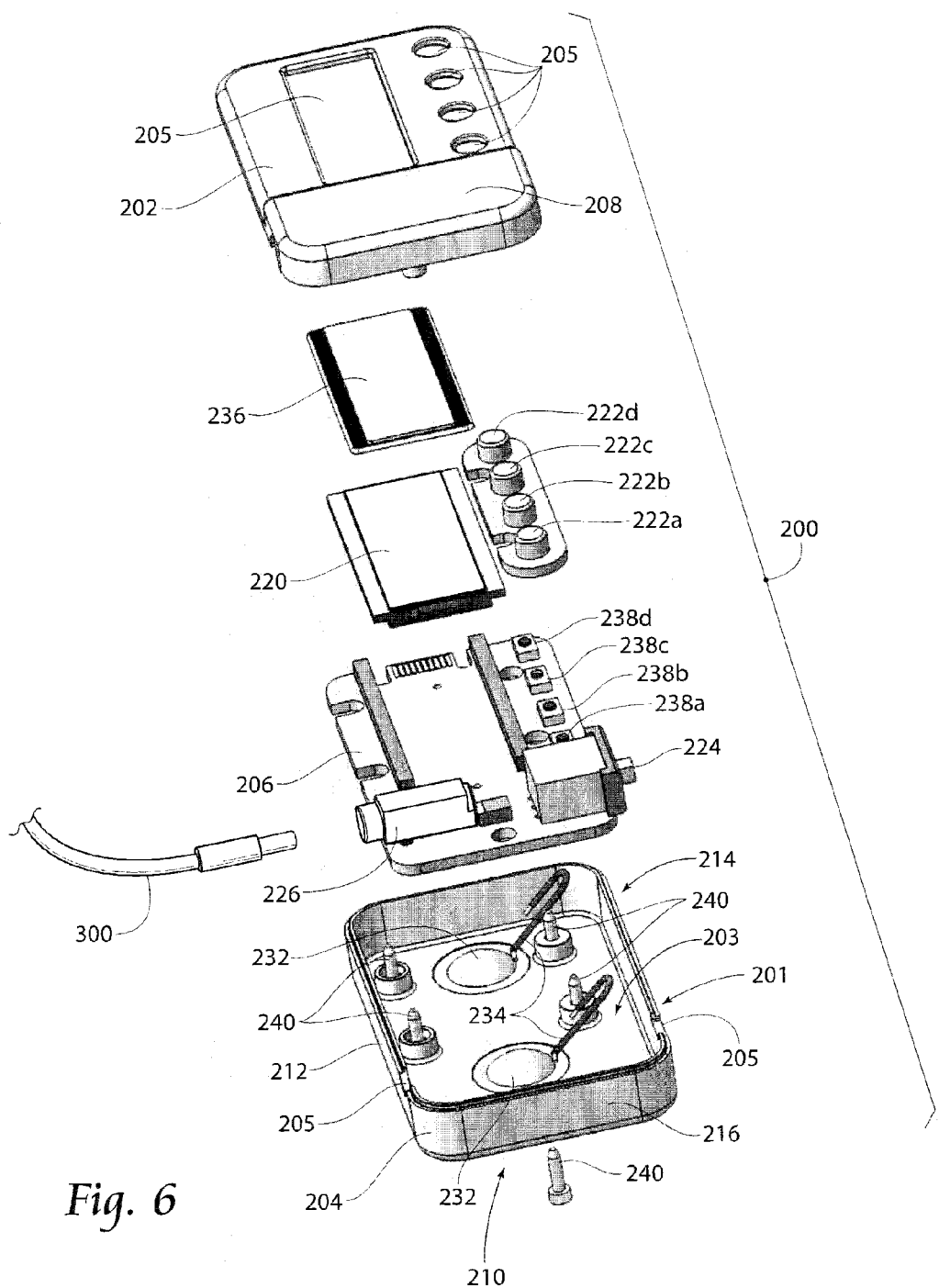
FIG. 6 is an assembly view of the embodiment of FIG. 5A.

Turning to FIG. 6, various circuit elements of a preferred stimulator 200 may be understood. As described, a preferred stimulator 200 includes two female parallel spring snaps 232 that mate with the two male snaps 122,132 on a preferred patch assembly 100 in either orientation, regardless of polarity. A battery power rectifier 250 provides a low loss circuit that takes either polarity of connection to the patch assembly 100 and completes an electrical connection between the conductive layer 104 and a ground connection of the stimulator circuitry and a positive battery terminal to the VBAT connection of the stimulator circuitry. This circuit element requires no external control or power and only needs connections to the battery and load.

A VCC power supply 252 provides power to a microcontroller 254. The microcontroller 254, and indirectly the LCD 220, the pushbutton and switch sensing circuitry, and a controlled current sink 256 of the output stage, all receive their power from the VCC power supply 252. The microcontroller 254 and the other circuit elements are designed to function correctly and within specifications over the entire range of acceptable battery voltages. The flash memory of the microcontroller 254, on the other hand, may be more sensitive to voltage variation, such as disallowing programming or erasure if VCC falls below 2.70 volts. Accordingly, the VCC power supply 252 includes circuitry to boost the battery voltage to about 3.3V, upon request by the microcontroller 254, when VCC directly generated from the battery voltage drops below 2.80V. The 0.10V difference between VCC=2.80V (where the VCC power supply begins boosting the battery voltage) e and VCC=2.70V (below which the microcontroller 254 cannot reliably program its flash memory) ensures correct operation even with the tolerance with which the microcontroller 254 can measure VCC. Specifically, the VCC power supply 252 has two modes of operation: Battery Voltage Pass-through operation and Charge Pump operation.

The microcontroller 254 places the VCC power supply 252 in the battery voltage pass-through mode at all times except when the sensed battery voltage is less than 2.80V and a flash memory erase or write operation may be required. In this pass-through mode, the battery voltage is connected directly to VCC through turned ON MOSFET switches. This allows an efficient generation of VCC with very little power loss.

The microcontroller 254 places the VCC power supply 252 in the charge pump mode only when sensed battery voltage is less than 2.80V and a microcontroller flash memory write or erase operation is likely required. In this charge pump mode, the VCC power supply 252 has a significant current drain in addition to the VCC current. Accordingly, this mode is preferably only used when required and represents a very small percentage of the total operating time of the stimulator 200.

An example of a microcontroller 254 that may be used in the stimulator 200 is a Texas Instruments MSP430FG437.

The microcontroller 254 uses preferably embedded firmware that controls the operation of the stimulator 200. The firmware is preferably saved in non-volatile (flash) memory which preferably cannot be modified by the end user of the device. In addition to the operating program stored in the flash memory, stimulus parameters programmed for and end user patient and the history of usage and errors are also preferably stored in other sections of the flash memory. The microcontroller 254 is responsible for the control of essentially all of the controllable electronic hardware of the stimulator 200: the sequence and timing of stimulus generation, interactions with user via slide switch, pushbutton, and the LCD screen, and for monitoring operation of the hardware to identify failures or unsafe operation.

The microcontroller 254 includes connections to a 32.768 KHz quartz crystal 258, which provides a precise clock source. This precision clock source is used to time the slower stimulus features (interval between pulses, duration of burst and gap, etc.). It is also used as part of a frequency-locked-loop to ensure that the high speed clock of the microcontroller 254 is correctly calibrated. This high speed clock is used to time the stimulus pulse duration, the interphase delay, and the relatively short times required for hardware activation, deactivation, settling, etc. Preferred pulse durations may be on the order of about 20 microseconds to about 200 microseconds. Most of these timing functions make use of timer hardware inside the microcontroller 254 that enables precise timing, including the generation of hardware I/O logic changes without software intervention after the timer is configured.

A 12-bit ADC (analog to digital converter) is provided in the microcontroller 254 and is used to measure VCC (and thus the battery voltage), the value of VCC when the charge pump is enabled, the value of the heavily filtered battery voltage driving a VHH power supply 260, and the value of VHH before, during, and after each stimulus pulse. These conversions are made using an external voltage reference 262 as either the reference for the conversion or the input using VCC as the reference for the conversion. This allows the precise measurement of these analog signals even with varying battery voltages.

Two 12-bit DAC (digital to analog) outputs are also provided by the microcontroller 254 and are used to program the requested voltage for the VHH Power supply 260 and to program a requested cathodic phase current generated by the controlled current sink 256.

The microcontroller 254 preferably automatically drives the segments and two backplanes of the LCD 220 taking segment values (on or off) and generating the necessary segment and backplane voltages for a preferably ½ duty cycle multiplexed LCD. The microcontroller 254 can also make small changes to LCD biasing voltages to correct for changes in battery voltage or ambient temperature if necessary.

The lockout slide switch 224 and the one or more, preferably four, momentary contact pushbuttons 238 are logic inputs to the microcontroller 254 (preferably provided with software de-bouncing the switches).

The VHH power supply 260 is enabled by the microcontroller 254 (via logic control lines) and charges to a voltage set by the microcontroller 254 (via a DAC output signal). The VHH power supply 260 is a low power boost DC-DC converter with a single inductor. The VHH power supply 260 is unique in that under microcontroller control (and timing) the VHH power supply 260 can be activated (generating the requested voltage), deactivated (not actively generating VHH, but holding VHH up with a nominal 1.8 µF of output capacitance), or floating (in which case the VHH is not actively being generated and is held up by only about 1 nF of output capacitance). This unique design can be used to generate the stimulus current waveform as described below. The VHH power supply 260 may use a Linear Technology LT1615-1 as the SMPS (Switch Mode Power Supply) chip with a Schottky diode for rectification.

The SMPS chip has a relatively large (330 µF) bypass capacitor on its input voltage pin that provides the energy necessary for generating VHH. The source resistance of some lithium batteries provides a basis for using the large bypass capacitor, averaging the 100 mA peak current required by the SMPS to 1 mA to 2 mA from the battery. A MOSFET switch isolates the large bypass capacitor from the battery, and two microcontroller IO pins with series resistors charge the large capacitor slowly to the battery voltage before the discrete MOSFET is enabled.

A low power precision voltage reference 262 (which may be a Texas Instruments REF3012) is provided with power by I/O pins of the microcontroller 254 acting as power output lines. This is possible because of the low operating current of this voltage reference. The reference voltage is used to make analog voltage measurements with the 12-bit ADC of the microcontroller 254 and to set the voltage of VHH and the stimulus amplitude (cathodic phase current) through the two DAC outputs. A preferred stimulus amplitude ranges from about 0.1 milliamp to about 20 milliamps, preferably configurable in increments of 0.1 milliamps to 1 milliamp.

A controlled current sink circuit 256 is a closed loop circuit using an N-channel MOSFET inside a feedback loop of an operational amplifier with logic shutdown control. The microcontroller 254 first provides power to the circuit (i.e., to the op amp) and sets the desired current level via a DAC signal. The microcontroller 254 then generates precisely timed pulse to enable the operational amplifier and to sink the specified amplitude from VHH to circuit common, or circuit ground.

Figure 7:
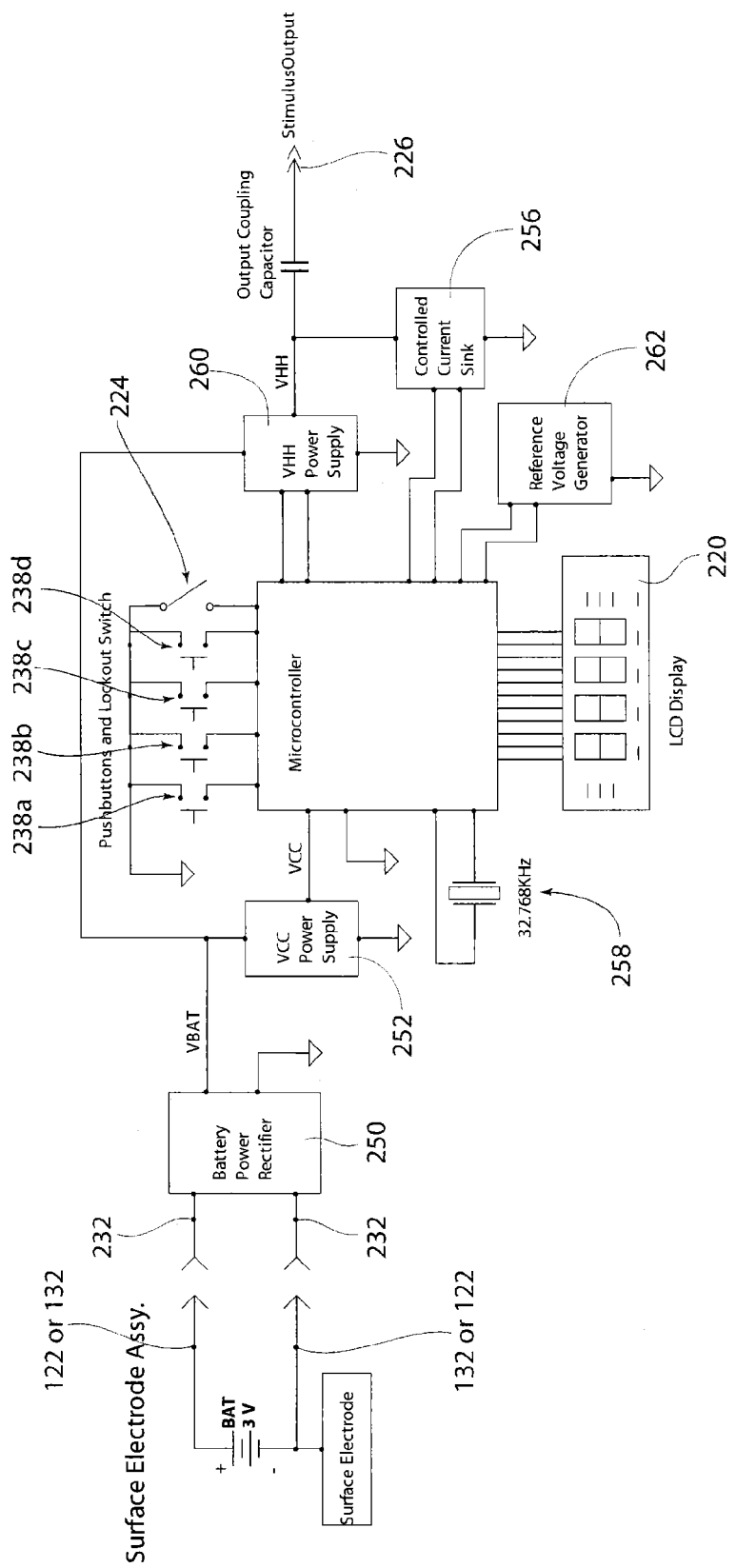
FIG. 7 is a block level schematic representation of electrical stimulation generation circuitry provided in the embodiment of FIG. 5A, further coupled to a schematic representation of the patch battery assembly of FIG. 4C.

FIG. 7 depicts a waveform of a preferred electrical stimulus current, which is preferably a biphasic, controlled current cathodic phase with an interphase delay interval of 100 µsec and a capacitor coupled recovery phase. The stimulus current, which is provided preferably at a frequency of about 5 Hz to about 25 Hz, is generated by the following operating conditions and sequence of events:

During stimulation and in the gaps between stimulus pulses, VHH is held up by the switched 1.8 µF output filter capacitor of the VHH power supply 260.

The VHH SMPS is periodically enabled to keep VHH near its desired value. VHH slowly discharges through the resistive voltage dividers of the SMPS and the VHH voltage sampling circuit.

The output coupling capacitor, a nominal 1.8 µF, is normally charged to VHH.

Preferably immediately before a stimulus pulse, the 1.8 µF output filter capacitor of the VHH power supply is isolated (disconnected from the circuit).

When the controlled current sink 256 is enabled for the stimulus pulse duration, the current comes from the output coupling capacitor passing current through the patient electrode circuit. This discharges the capacitor by Q/C (a little more than 2V for the maximum charge stimulus pulse).

During the interphase delay interval, the controlled current sink has been disabled and there is not significant current flow through the patient circuit.

At the beginning of the recovery phase, the output filter capacitor of the VHH power supply is again enabled (returned to the circuit) and then the VHH SMPS is enabled, pulling VHH back to its original value and returning the charge from the patient circuit.

Hardware-Software Partitioning & Software Detection of Hardware Failures

Refreshing and multiplexing of the segments and backplanes of the LCD 220 is preferably accomplished by the microcontroller 254 and a resistor divider network. The generation of the cathodic phase current (i.e., enabling the controlled current sink 256) is preferably started and stopped by timer hardware within the microcontroller 254. Sampling of the VHH during the cathodic phase is also preferably invoked by timer hardware of the microcontroller 254. The hardware is preferably configurable and configured by software, as is the overall timing and sequencing of hardware to make stimulus pulses with desired timings for ramp, burst, ramp, and gap sequence portions.

The operating software is also preferably responsible for periodic monitoring of hardware status to ensure that the stimulator 200 is operating correctly and without hardware failures that have safety implications. Various specific monitoring may be desirable, e.g.:

- At power ON, the integrity of the flash memory may be tested and verified. If the flash memory may have been corrupted, the stimulator 200 may prevent enablement of VHH generation and will remain OFF.
- At power ON, the integrity of microcontroller RAM memory may be tested and verified. If the RAM memory is not functional, the stimulator 200 may prevent enablement of VHH generation and will remain OFF.
- VCC (Battery Voltage) may be measured before every stimulus pulse and stimulation may be suspended if the battery voltage is inadequate to ensure the pulse will be safely generated by the charge already in the 330 µF input filter capacitor of the VHH power supply 260.
- VCC may be measured before each write or erase of flash memory that may require the operation of the charge pumped VCC. Stimulation may be suspended if the value is outside specified limits.
- The value of VHH may be measured before, during and/or after each stimulus pulse. These voltages may be tested to confirm that the VHH voltage measured is within specifications of the voltage requested. If the voltage is outside of a desired range of acceptable values, stimulation may be suspended and VHH may be shutdown. These voltages may also be tested to detect an open electrode circuit, which also preferably suspends stimulation and shuts down VHH. Lastly, the sag in VHH between stimulus pulses (or between refresh cycles that bring VHH back up to the desired value) may be measured to verify that current is not flowing (potentially through the patient) when it should not be.

Figure 8:
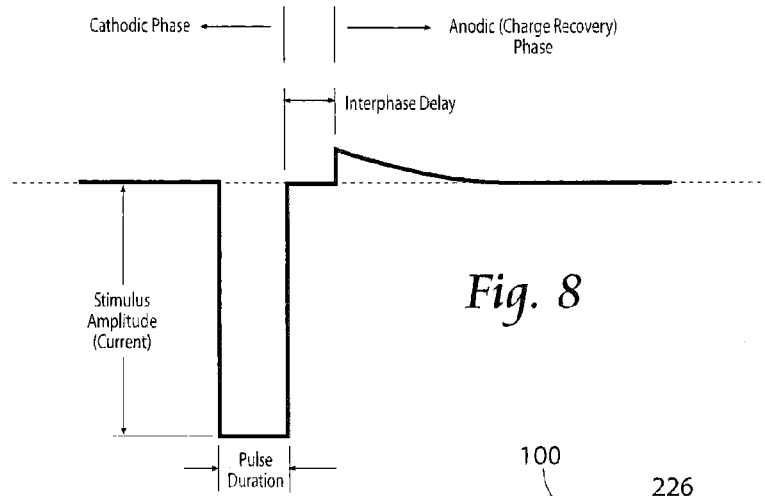
FIG. 8 is an embodiment of a waveform to be generated by stimulation pulse generation circuitry according to the present invention.

FIG. 8 depicts a stimulator 200 according to the present invention mechanically mounted to a patch assembly 100 according to the present invention.

Cables

Figure 9:
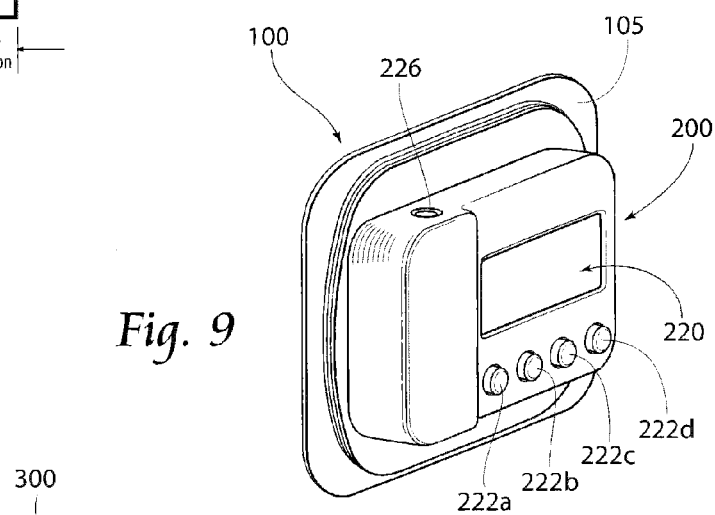
FIG. 9 is a perspective view of the electrical stimulator of FIG. 5A physically and electrically coupled to the patch assembly of FIG. 3.
Figure 10:
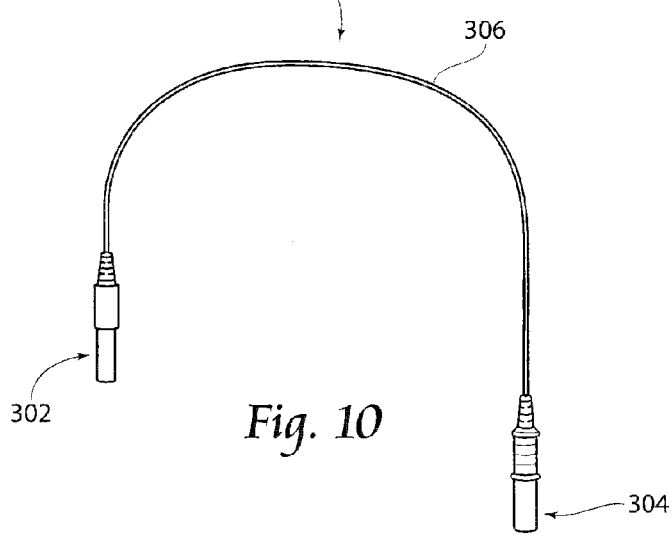
FIG. 10 is an elevation view of a first embodiment of a cable according to the present invention.
Figure 11:
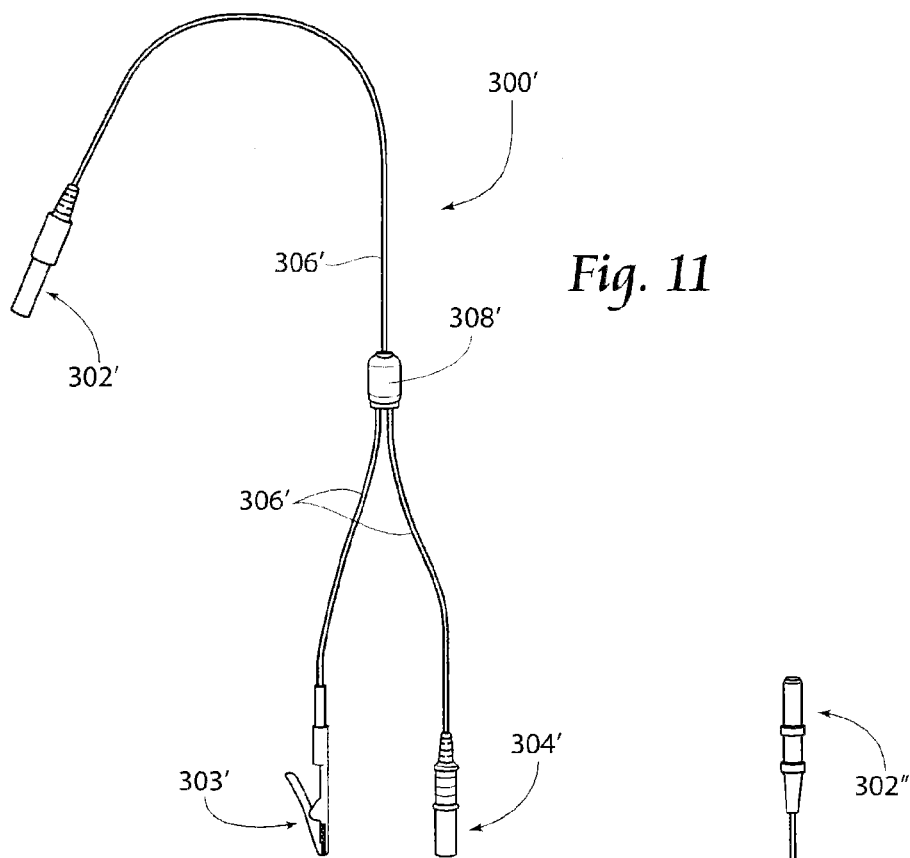
FIG. 11 is an elevation view of a second embodiment of a cable according to the present invention.
Figure 12:
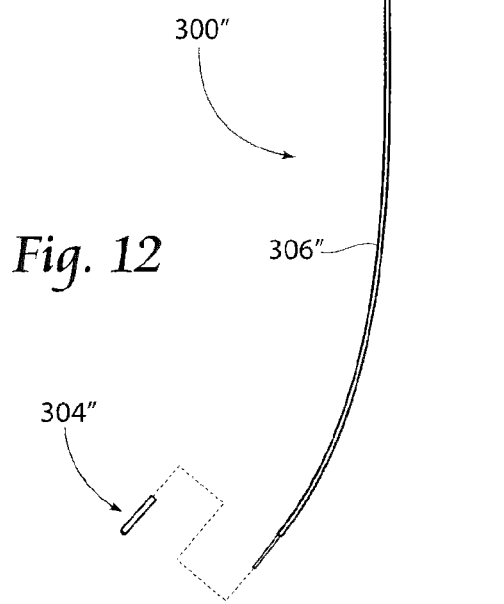
FIG. 12 is an elevation view of a third embodiment of a cable according to the present invention.
Figure 13A:
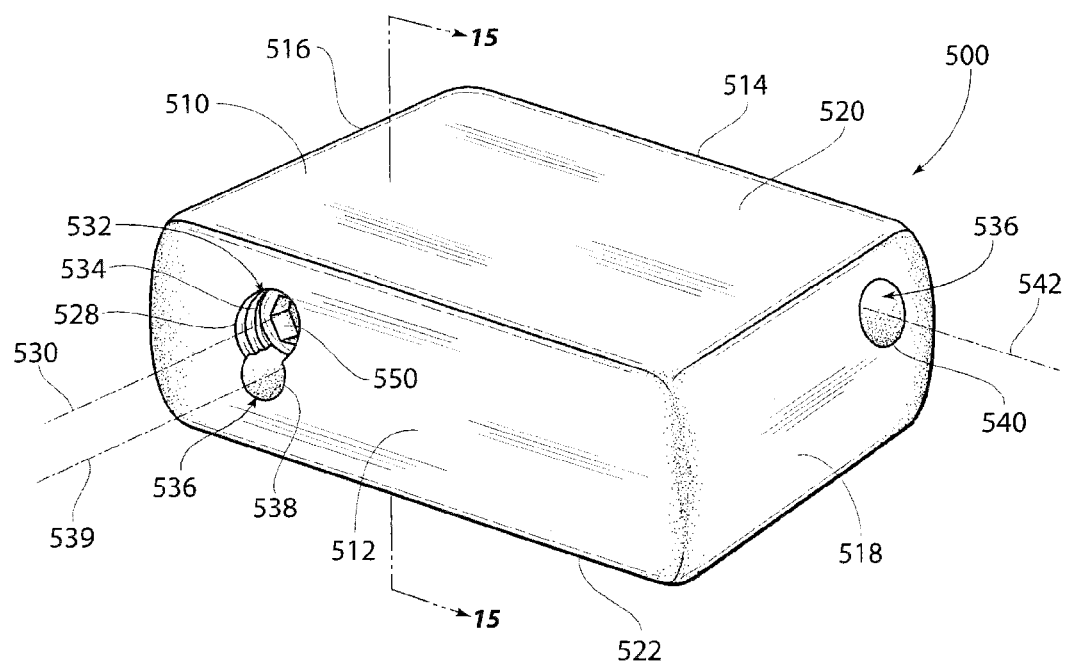
FIG. 13A is a perspective view of a first embodiment of an insulation displacement connector according to the present invention.
Figure 13B:
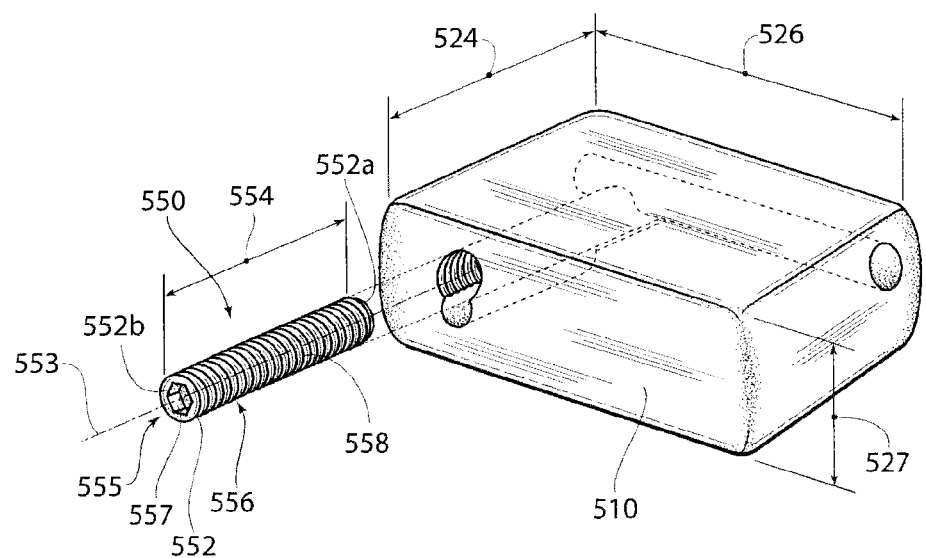
FIG. 13B is a partial assembly view of the connector of FIG. 13A.

FIGS. 9-11 depict various cable embodiments 300 according to the present invention. A first cable embodiment 300, shown in FIG. 9, generally includes a single conductive path extending between and including a first connector element 302 and a second conductor element 304. The first connector element 302 is preferably a touchproof pin connector having a conductive pin of a first diameter, such as about 1.0 millimeter. The second connector element 304 is preferably also a touchproof pin connector having a conductive pin of a second diameter, which is preferably different from the first diameter, such as being greater than the first diameter. The second diameter is preferably about 1.5 millimeters. The provision of different connector pin diameters is preferred to aid in preventing reversal of the cable 300 during use. Additionally, the first connector element 302 may be provided as a first color, such as a color that corresponds to a color of the stimulator housing 201, such as white, and the second connector element 304 may be provided as a second color, which is different from the first, the second color being, e.g., black. The pins in the connector elements 302,304 are preferably electrically connected by an insulated electrical wire 306 disposed therebetween. A preferred insulated wire 306 may be a single tinsel wire (nominal resistance of about 0.20 ohms/foot) having a preferred overall diameter of about 50 mils and a preferred nominal tensile break strength of about 33 pounds. The cable 300 may be provided along a preferred length end-to-end, such as about thirteen to about fifteen inches. Multiple embodiments of the first cable 300 may be provided in a kit so as to provide different lengths of the cable 300, such as about six inches. The first connector element 302 is preferably mateable with the jack 226 provided on the stimulator 200. The second connector element 304 may be mateable with an intermediate cable (such as intermediate cable 300" described below) or directly with a percutaneous lead 400.

A second cable embodiment 300', shown in FIG. 10, generally includes a single conductive path extending between and including a first connector element 302', a second conductor element 303', and a third connector element 304'. The first connector element 302' is preferably a touchproof pin connector having a conductive pin of a first diameter, such as about 1.0 millimeter. The second connector element 303' is preferably an alligator clip, which may be provided in a desirable color, such as red. The third connector element 304' is preferably also a touchproof pin connector having a conductive pin of a second diameter, which is preferably different from the first diameter, such as being greater than the first diameter. The second diameter is preferably about 1.5 millimeters. The provision of different connector pin diameters is preferred to aid in preventing reversal of the cable 300' during use. Additionally, the first connector element 302' may be provided as a first color, such as a color that corresponds to a color of the stimulator housing 201, such as white, and the third connector element 304' may be provided as a second color, which is different from the first, the second color being, e.g., black. The pins in the connector elements 302',304', and the second connector element 303', are preferably electrically connected by insulated electrical wire 306' disposed therebetween and spliced by a bifurcation connector 308'. A preferred insulated wire 306' may be, e.g. a 24 gauge stranded copper wire (nominal resistance of about 0.03 ohms/foot) having a preferred overall diameter of about 50 mils and a preferred nominal tensile break strength of about eleven pounds. The wire 306' may be provided along a preferred length between the first connector element 302' and the bifurcation connector 308', such as about fifteen to about sixteen inches. The first connector element 302' is preferably mateable with the jack 226 provided on the stimulator 200. The third connector element 304' may be mateable with an intermediate cable (such as intermediate cable 300" described below) or directly with a percutaneous lead 400.

FIG. 11 provides an intermediate cable 300" according to the present invention. The intermediate cable 300" generally includes a single conductive path extending between and including a first connector element 302", and a second connector element 304". The first connector element 302' is preferably a touchproof pin receiver connector (or touchproof female connector) having a conductive sleeve adapted to receive a pin of a first diameter, such as about 1.5 millimeters. The second connector element 304" is preferably a crimpable termination connector, such as a piece of stainless steel tubing material having an external diameter of about 50 mils and an internal diameter of about 42 mils, or 18 gauge. The connector elements 302",304" are preferably electrically connected by insulated electrical wire 306" disposed therebetween. A preferred insulated wire 306" may be, e.g. tinsel wire, having a preferred overall diameter of about 50 mils. The wire 306" may be provided along a preferred length end-to-end, such as about seven to about nine inches. The first connector element 302" is preferably mateable with a touchproof pin connector, such as connector element 304 or 304', previously described. The second connector element 304", after being crimped onto a stripped portion of the wire 306", is preferably mateable with an insulation displacement connector 500 as hereinafter described, or directly with a percutaneous lead 400.

Cable Connector

With reference to FIGS. 12A-15, a preferred insulation displacement connector 500 may be described. Such connector may be found in U.S. patent application Ser. No. 12/958,077, filed on Dec. 1, 2010, which is incorporated by reference herein in its entirety. The connector 500 generally includes a connector body 510 and a coupling element 550. The connector body 510 may be formed of any desirable shape, but is preferably formed substantially as a parallelepiped having a front surface 512 oppositely disposed from a rear surface 514, a left surface 516 oppositely disposed from a right surface 518, and a top surface 520 oppositely disposed from a bottom surface 522. The front surface 512 may be situated at a body width 524 from the rear surface 514, the left surface 516 may be situated at a body length 526 from the right surface 518, and the top surface 520 may be situated at a body thickness 527 from the bottom surface 522. The body width 524 is preferably about 0.25 inches to about 0.75 inches, more preferably about 0.30 inches to about 0.50 inches, and most preferably about 0.40 inches. The body length 526 is preferably about 0.50 inches to about 1.00 inches, more preferably about 0.50 inches to about 0.75 inches, and most preferably about 0.625 inches. The body thickness 527 is preferably about 0.15 inches to about 0.50 inches, more preferably about 0.20 inches to about 0.30 inches, and most preferably about 0.25 inches.

While the connector body 510 may be formed of any desirable material that may be selected for a given use, the connector body 510 is preferably formed from an electrically insulative material, such as a thermoplastic material, which may be a USP Class VI medical grade plastic material. A preferred material may be selected from the Ultem® family of amorphous thermoplastic polyetherimide (PEI) available from Sabic Innovative Plastics Holding BV, of Pittsville, Mass., and also of the Netherlands. A preferred material is Ultem 1000. Indeed, the connector body 510 may be machined from Ultem bar stock having a desired diameter, such as about 0.625 inches, which may cause the left surface 516 and right surface 518 to be generally convex along the body width 524.

Formed into the connector body 510 is at least one engagement aperture, bore or channel 528, formed along an engagement axis 530. The engagement aperture 528 is provided with an engagement means 532, such as threads 534, to cooperate with the coupling element 550. The engagement aperture 528 may be formed through the connector body 510, such as through the entire width 524, as shown. The threads 534 may be formed during casting of the body 510 or in a machining process after the body 510 has been cast or machined.

Also formed into the connector body 510 is at least one conductor aperture, bore or channel 536. In the embodiment shown, a first conductor channel 538 is formed into the front surface 512 of the connector body 510, the first conductor channel 538 being formed along a first conductor axis 539 which may be disposed at least substantially parallel to the engagement axis 530. The first conductor channel 538 is preferably a smooth reentrant bore, which is formed at a distance from or relation to the engagement aperture 528 so as to intersect the engagement aperture 528. As shown, the first conductor axis 539 is disposed substantially parallel to the engagement axis 530, and spaced therefrom by a distance that is preferably less than the sum of the radius of each of the axes 530,539 such that the first conductor channel 538 overlaps the engagement aperture 528 longitudinally along a length thereof. A portion 538a of the first conductor channel 538 preferably extends through the connector body 510, and such arrangement may be desirable to provide for conductor length adjustment. The portion 538a may extend substantially directionally perpendicularly to a tangent of threads 558 provided on the stud 552, as further described below.

In the first embodiment 500, a second conductor aperture, bore or channel 540 is formed along a second conductor axis 542. While the second conductor bore 540 may extend through the entire connector body 510, such as through the entire body length 526, the second conductor bore 540 is preferably a smooth reentrant bore, which at least partially intersects the engagement aperture 528. The second conductor axis 542 may be coplanar with the engagement axis 530, but is preferably perpendicularly skew to the engagement axis 530 at a desired angle. Thus, in the embodiment 500 shown, using the engagement axis 530 as a reference, the first conductor axis 539 is disposed substantially parallel to and below the engagement axis 530, while the second conductor axis 542 may be disposed perpendicularly skew to and above the engagement axis 530. The angle at which the second conductor bore 540 may be formed skew to the engagement axis 530 is preferably greater than 45 degrees and less than about 135 degrees, and is preferably about 90 degrees. However, as described in connection with later embodiments, the second conductor axis 542 may be disposed substantially parallel (about zero or about 180 degrees) to the engagement axis 530.

The coupling element 550 is preferably formed as a conductive stud 552 formed between a first end 552a and second end 552b along a stud axis 553 for a stud length 554. The stud length 554 is preferably less than a dimension of the connector body 510 that is parallel to the engagement axis 530. Indeed, when the coupling element 550 is operatively positioned to couple a plurality of conductors, the coupling element 550 is preferably situated completely within all perimeters of the connector body 510, so as to inhibit electrical conduction through the coupling element 550 through accidental outside contact. The stud 552 preferably has mating engagement means 556, such as threads 558, formed along at least a portion of the stud length 554, to cooperate with the engagement means 532 provided in the engagement aperture 528, such as at least a portion of the threads 534, provided in the engagement aperture 528. A preferred material for the stud 552 is stainless steel, copper, or any other conductive material. The first end 552 is preferably at least partially formed as a substantially planar surface disposed preferably orthogonally to the stud axis 553. The second end 552*b* is preferably provided with a tool engagement surface 555, which may include a female hexagonal socket 557, as shown, or other engagement surface.

To use the first embodiment 500 of a connector according to the present invention, a plurality of insulated conductors 306",400 are inserted into the connector 500, and electrically coupled by the coupling member 550. A first insulated conductor 306" may include an electrically conductive portion circumferentially surrounded by an electrically insulative portion. The conductive portion may be a solid conductor, such as a wire of suitable gauge, a plurality of conductors forming a straight stranded wire, or one or more coiled wires having an at-rest turns-per-inch count. Electrically coupled to the conductive portion is an electrically conductive terminal 304", such as a stainless steel terminal that may be crimped onto the conductor and/or the insulation, as described above. A second insulated conductor 400 may include a electrically conductive portion circumferentially surrounded by an electrically insulative portion. The conductive portion may be a solid conductor, such as a wire of suitable gauge, a plurality of conductors forming a straight stranded wire, or one or more coiled wires having an at-rest turns-per-inch count, and is preferably the latter. At an end of the second conductor 400 distal from the connector 500, the conductor 400 may terminate in a desired fashion, such as with a custom or conventional electrical plug, socket, jack, etc., or with a functional termination such as a stimulating electrode 402, and more preferably a stimulating electrode configured to be anchored in animal tissue.

Figure 14:
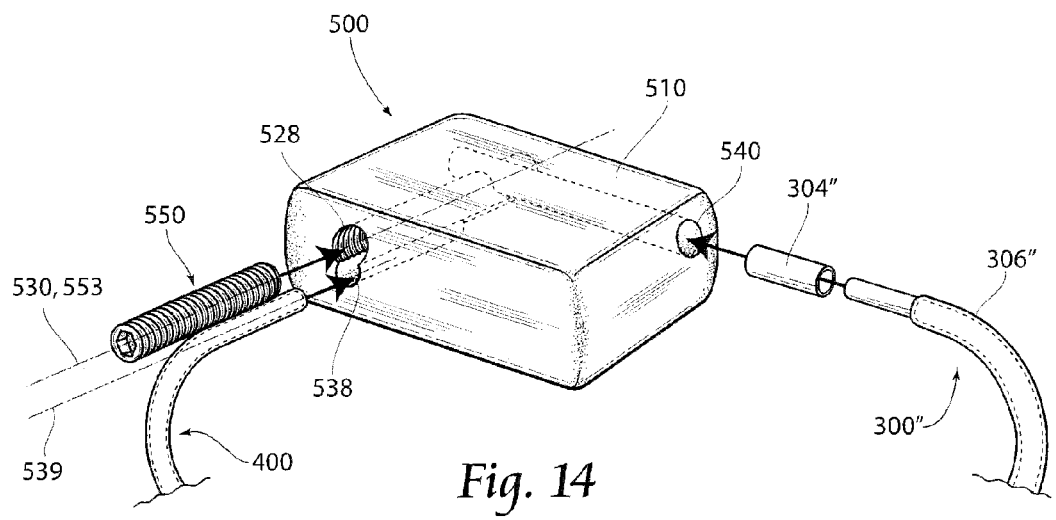
FIG. 14 is a second partial assembly view of the connector of FIG. 13A.
Figure 15:
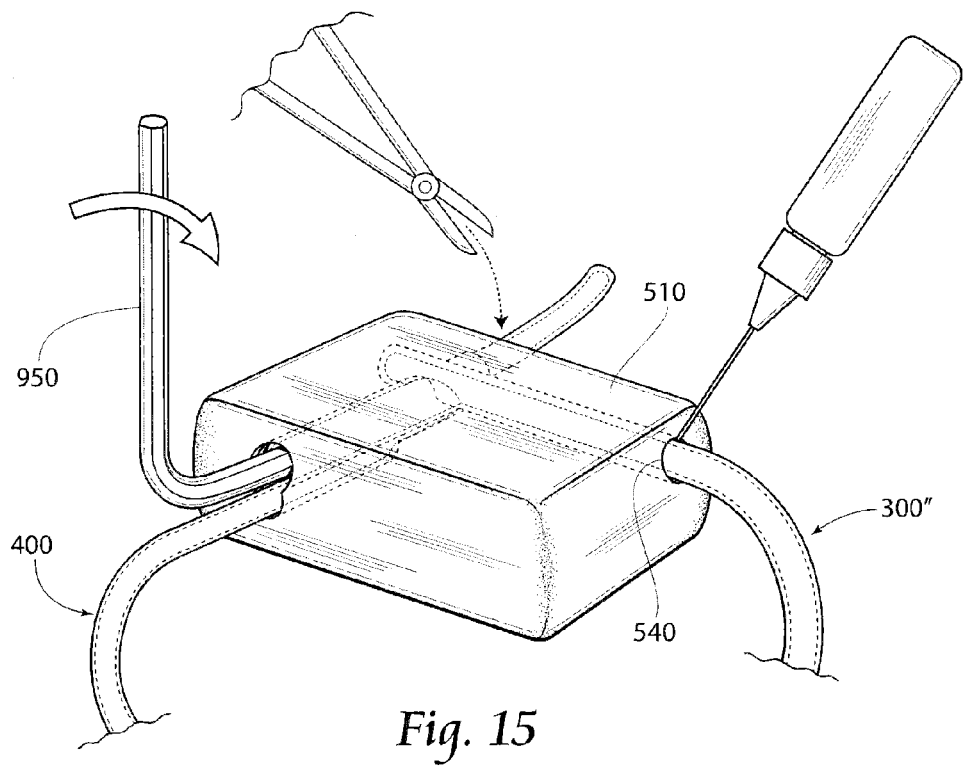
FIG. 15 is a first perspective view of the assembly of FIG. 14 further assembled.

To use the connector 500, the first conductor 306" is inserted into the second conductor bore 540 such that the terminal 304" is disposed at least partially within the engagement aperture 528. Preferably, the terminal 304" abuts a closed end of the second conductor bore 540 to register the terminal 304" in a desirable position to help reduce guesswork as to positioning. The first conductor 306" may be secured to the connector body 510, such as with adhesive or sealant, or with a nonpenetrating set screw. Preferably, along at least a portion of the second conductor bore 540, void space that may exist between the insulated wire 306" and the bore 540 is at least partially filled with an electrically insulative substance, such as silicone. The process of disposing the first conductor 306" at least partially within the connector body 510 may be performed generally prior to product packaging, such as sterile product packaging, or such assembly may be performed by a user upon opening one or more sterile packages containing the first conductor 306" and the connector body 510. Preferably, though not necessarily, after the first conductor 306" is inserted and/or positioned, the second conductor 400 is preferably inserted into the first conductor channel 538 and at least partially into the engagement aperture 528. If the engagement aperture 528 extends entirely through the connector body 510, the second conductor 400 may be pulled through the body 510 to a desired length. Once the conductors 306",400 are at a desired position, the coupling member 550 is placed into electrical communication with both conductive portions of the wires 306",400. While the coupling member 550 may be completely removed from the body 510 to allow insertion of the second conductor 400, the coupling member 550 is preferably prepositioned at least partially within the engagement aperture 528 prior to the insertion of the second conductor 400. Such prepositioning may be done generally at the time of manufacture, and the member 550 may be held substantially rotationally stationary in the engagement aperture 528 by, for example, a drop of silicone. One way in which such electrical communication may be achieved is by the threads 558 cutting through the insulation of the second conductor 400 and the first end 552*a* abutting the terminal 304" of the first conductor 306". The stud 552 may be advanced, such as with a standard L-shaped hex, or other wrench 950 (as shown in FIG. 14), in the engagement aperture 528 to a desired position, such as for an instructed number of turns or to a desired torque. Some deformation or deflection of the terminal 304" may occur. Once operatively positioned, the stud 552 preferably is disposed completely within all perimeters of the connector body 510.

As mentioned, the conductors 306",400 may be one or more coiled wires having an at-rest (unstretched) turns-per-inch count. The threads 558 on the coupling member 550 are preferably positioned at a thread pitch that approximates (preferably +/−10%) the at-rest turns-per-inch count of a (multi-)coiled conductor, if used.

Connector Mounting Structure

Figure 16:
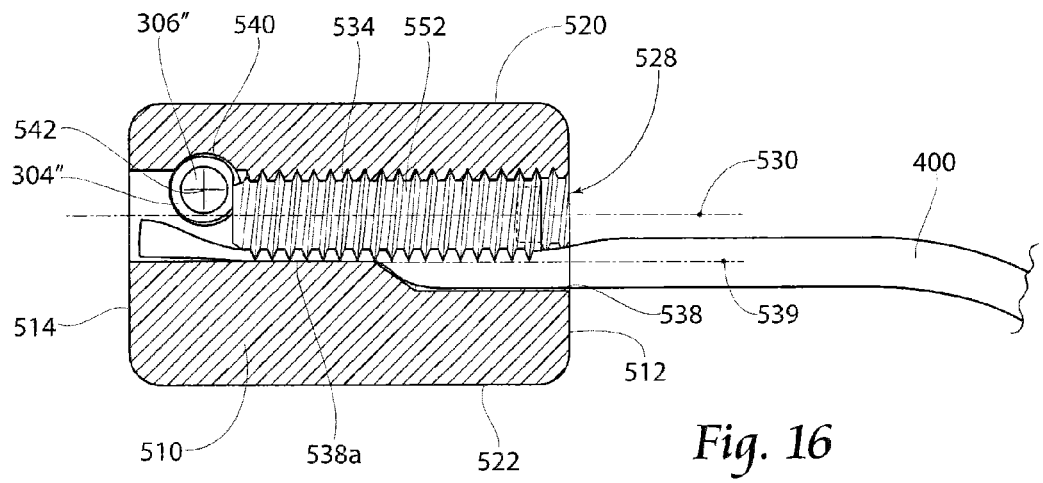
FIG. 16 is a cross-section view taken along line 16-16 of FIG. 13A, further showing conductors installed.

Turning now to FIG. 16, a preferred connector mounting structure 600 is shown. The preferred connector mounting structure 600 includes a generally planar connector mounting pad 602 adhered to a generally planar pad carrier 604. The connector mounting pad 602 is preferably a polyethylene tape material, that may be coated with adhesive on two sides. The pad carrier 604 is preferably formed from a polyester nonwoven tape that is coated with an adhesive on a single side. The mounting pad 602 is preferably adhered to the side of the pad carrier 604 that does not include adhesive. The connector mounting structure 600 also preferably includes a connector cover strap 608, which is preferably formed from a polyolefin tape material coated on a single side with adhesive. The cover strap 608 is preferably adhered to the pad carrier 604, preferably on the side of the pad carrier that does not include adhesive. A releasable liner 610 may be provided in a V-formation, with one side of the V adhered to the cover strap 608 and the other side of the V adhered to the mounting pad 602. Provided on the side of the carrier 604 that is preferably provided with adhesive may be a substantially planar cushion pad 612, which is preferably a polyethylene foam tape material, which may be provided with adhesive on a single side. The substantially planar side of the cushion pad 612 provided with adhesive is preferably mated with the side of the carrier 604 that is provided with adhesive. Generally, the cushion pad 612 is provided along a substantially similar or identical length of the carrier 604 as the connector pad 602 is provided on the opposite side of the carrier 604. Also disposed on the adhesive side of the carrier 604 is a pair of preferably overlapping release liners 614, which preferably overlap across at least a portion of the cushion pad 612. At least one of the release liners 614 preferably extends longitudinally beyond an edge of the carrier 604 to aid in starting to release the liner from the carrier 604. To use the connector mounting structure 600, the release liner 610 may be removed from the connector pad 602, and an electrical connector, such as connector 500, may be secured thereto by the adhesive provided thereon. The release liner 610 may be further removed from the cover strap 608, and the adhesive side of the strap 608 may overlie and adhere to the connector 500 and the carrier 604. The connector mounting structure 600 may then further be mounted to a support structure, such as an external skin surface of a human user patient. The release liners 614 may be removed from the adhesive side of the carrier 604, and the carrier 604 may be adhered to the skin surface, with the cushion pad 612 lying in intimate contact with the skin surface. Of course, a connector mounting structure according to the present invention may be constructed without the cushion pad 612, and would still fall within the contemplated scope of the invention.

Percutaneous Lead

Figure 17:
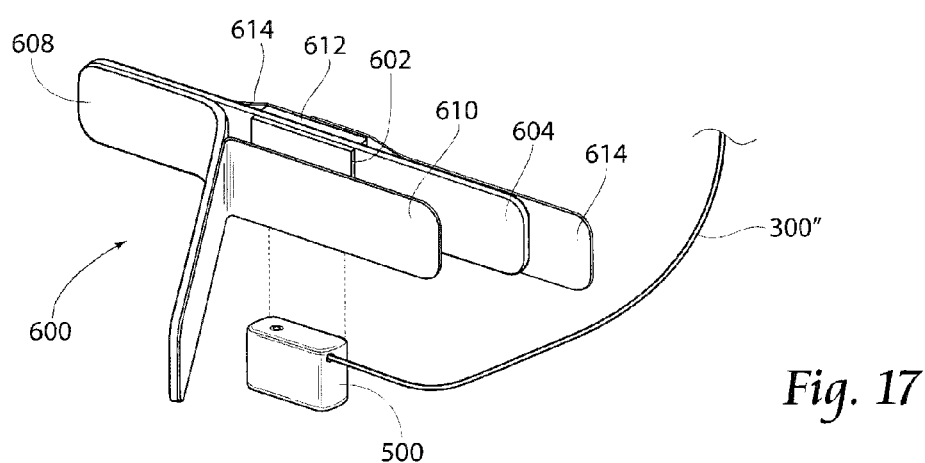
FIG. 17 is a perspective view of an embodiment of a connector mounting structure according to the present invention.

Turning now to FIG. 17, a preferred percutaneous lead 400 may be described. The lead 400 preferably includes an electrode 402 that extends from preferably an insulated conductor 404 having an insulated diameter 406 of about 10 mils. The insulated conductor 404 is preferably 4250 PFA coated 7-strand 316L stainless steel, which is preferably wound about a mandrel to form an insulated coiled portion 408 of a desired length, such as about seven to about nine inches. A portion of a distal end of the conductor 404 is stripped to form the electrode 402. The stripped portion is preferably coiled on a mandrel to an outside diameter of about 10 mils to about 15 mils, and then bent at an electrode angle 410 of about 20 degrees to about 70 degrees. The electrode 402 includes an extension 412 and a barb 414. The extension 412 has an electrode extension length 416 of about 350 mils to about 450 mils, and the barb 414 has a barb length 418 of about half that of the extension length 416, of about 160 mils to about 240 mils. At the juncture of the electrode 402 and the coiled insulated portion 408, a fillet of silicon adhesive 419, such as Nusil Med 1511, is preferably provided circumferentially about the lead 400. A test portion 420 of a proximal end of the lead 400 may also be stripped and tinned, and a maximum end-to-end resistance of the lead 400 is preferably about 150 ohms. Provided at a tip 422 of the barb 414 of the electrode 402 is preferably a weld to maintain the conductors of the lead 400 in a desired position. An electrically conductive path in which the lead 400 is used preferably has a maximum resistance of about 1300 ohms.

Figure 18:
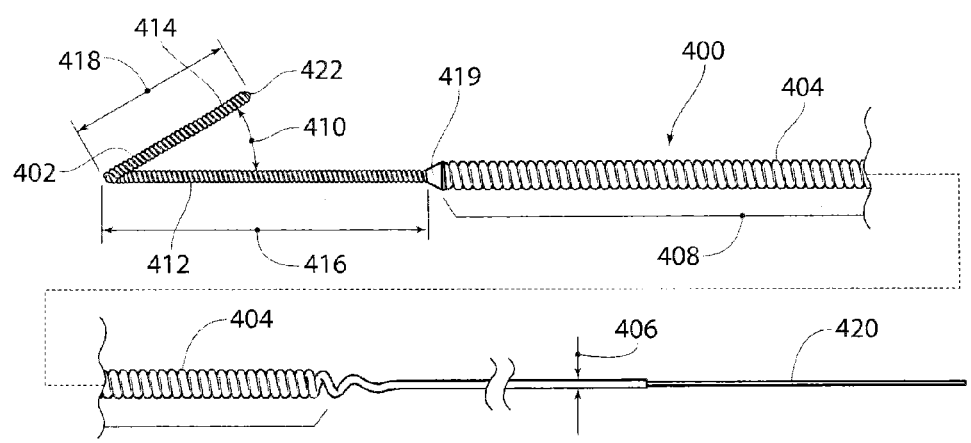
FIG. 18 is an elevation view of an embodiment of a percutaneous lead according to the present invention.

The lead 400 described may be used percutaneously, i.e. introduced through the epidermis of an animal. To accomplish such introduction, a lead introducer 700 may be used, such as that shown in FIG. 18. The introducer 700 extends from a proximal end 702 to a distal end 704, with a lumen 706 extending therethrough. Provided at the proximal end 702 may be preferably a locking Luer hub 706, which may be electroless nickel plated brass 360 having a Luer taper conforming to ISO 594-1:1986. Extending from the hub 706 towards the distal end 704 is an introducer needle 708 made from 20 gauge 304 full hard stainless steel thin wall hypodermic tubing with an outside diameter of about 35 to about 36 mils and an inside diameter of about 25 to about 30 mils. The Luer hub 706 and needle 708 are preferably coated with 0.1 to 0.2 mils of electrically insulative SCS Parylene C conformal coating applied to external surfaces. The electrically insulative coating preferably provides at least 100 volt minimum dielectric strength. A plurality of depth markings 710 are preferably provided along the length of the needle 708. Preferably, twelve such markings 710 are provided at a spacing of about 400 mils. The markings 710 may be formed, e.g., by laser etching. At the distal end 704, the needle 708 is preferably ground to a three-face lancet formation, including a point 712, a bevel portion 714, and a non-coring heel portion 716. The cuts to form the bevel 714 and heel portion 716 are all preferably provided at an angle of about 18 degrees from longitudinal parallels to the exterior surface of the needle 708.

Percutaneous Lead Placement

FIG. 19 depicts the percutaneous lead 400 having been inserted into the introducer 700 for use. It may be desirable to provide a protective plastic tubular member 720 disposed over the introducer needle 708 for packaging and safety purposes. Physician experience with placing needles in muscle using standard locations for clinical electromyography or near peripheral nerves using standard procedures for nerve block (regional anesthesia) may be recommended. Lead and/or needle advancement is preferably to be stopped approximately 0.5-1 cm proximal to the depth that is traditionally used in standard needle insertion techniques. Imaging, such as ultrasound, may be useful during the procedure.

Conventional needle electrodes may be used to deliver test stimulation before percutaneously placing a lead, such as the lead 400 previously described. Local anesthesia may be provided at the discretion of the clinician. Anesthesia may be applied subcutaneously (e.g., lidocaine), topically (e.g., EMLA cream), or both. It is preferable to not administer the local anesthetic too close to the target electrode site because doing so could affect the response to stimulation. With a user patient appropriately positioned, a lead entry site should be identified on the skin of the patient and cleaned with a standard prep solution to create a sterile field. A test stimulation may be delivered through a needle electrode for identification of a proper target lead placement position. The stimulator 200 may be mounted to the patch assembly 100. The patch assembly 100 may be adhered to the patient's skin, preferably outside of the sterile field. It is preferred to refrain from positioning the stimulator across the midline of the patient's body from the target electrode site to prevent inadvertently passing stimulation current across the heart. A target stimulation site is identified, such as a target peripheral nerve, and the needle electrode may be placed or attempted to be placed at the target site. The stimulator 200 may be connected to the needle electrode using a cable, such as the cable 300' previously described, by using the second connector element 303' or the third connector element 304'.

The stimulator 200 may be programmed to deliver a test stimulation to the needle electrode. Programming of the stimulator is further described below. With the stimulus amplitude and frequency set to desired levels and the pulse duration set to a desired floor value (such as about 20 μsec), stimulation may be initiated by pressing and releasing the Start/Stop button 222d. While stimulation is being delivered, the pulse duration may be slowly increased by slowly (e.g. once every one to twenty seconds, but more preferably once every five to ten seconds) serially pressing and releasing the Increase button 222c until a desired response to the stimulation is obtained. A desired response may include a desired paresthetic effect and/or comfortable muscle contraction in the target area. If a desired response to the stimulation is not obtained, the needle electrode may be repositioned as necessary, to a location that provides the desired response at a comfortable stimulus intensity. The location of the needle electrode may be identified and/or logged, or the needle electrode may remain in place, to guide placement of the electrode lead 400. Preferably during placement of the electrode lead 400, the cable 300' is disconnected from the needle electrode.

An anticipated pathway for the electrode lead 400 may be visualized by the clinician, either based on experience or based on the test stimulation previously applied, as described above. If desired, a local anesthetic may be administered subcutaneously, topically, or both at the insertion site for the electrode lead 400. Again, it is preferable to refrain from administering a local anesthetic too close to the target electrode site because doing so could affect the response to stimulation. With the electrode lead 400 situated within its introducer 700, as shown in FIG. 19, both may be introduced through the patient's skin towards the target stimulation site, which may have previously been identified by using the needle electrode. Preferably, a test stimulation may be delivered as the introducer 700 and lead 400 are advanced (at approximately 1 cm intervals) to optimize the electrode 402 location. To deliver test stimulation to the electrode 402, the second connector element 303' of the cable 300' may be clipped to the conductive proximal end of the lead 400 while the first connector element 302' may be electrically coupled to the stimulator 200, thus establishing a conductive path from the stimulation generation circuitry in the stimulator 200 to the electrode 402. As with the test stimulation applied to the needle electrode, the stimulator 200 may be programmed to deliver a test stimulation to the electrode 402. Programming of the stimulator is further described below. With the stimulus amplitude and frequency set to desired levels and the pulse duration set to a desired floor value (such as about 20 μsec), stimulation may be initiated by pressing and releasing the Start/Stop button 222d. While stimulation is being delivered to the electrode 402, the pulse duration may be slowly increased by slowly (e.g. once every one to twenty seconds, but more preferably once every five to ten seconds) serially pressing and releasing the Increase button 222c until a desired response to the stimulation is obtained. A desired response may include a desired paresthetic effect and/or comfortable muscle contraction in the target area. If a desired response to the stimulation is not obtained, the electrode 402 may be repositioned, e.g. advanced, as necessary, to a location that provides the desired response at a comfortable stimulus intensity. Once a desired response is obtained, the introducer 700 may be removed from the patient, such as by sliding the introducer needle 708 along the lead 400. It may be helpful to apply gentle manual pressure towards the location of the electrode 402 during withdrawal of the introducer 700. Another test stimulation may be applied to the electrode 402 to ensure that the lead 400 has not moved due to the removal of the introducer 700. At this time, the cable 304' may be disconnected from the lead 400 and the stimulator 200 and the patch assembly 100 and stimulator 200 may be removed from the patient's skin.

Lead Placement Near Peripheral Nerves

One goal of peripheral nerve stimulation may be pain relief. The following paragraphs provide more detailed instructions for placing the lead 400 near two nerves that may be targeted for pain relief: the axillary nerve (upper extremity example) and the femoral nerve (lower extremity example). These instructions are presented as possible approaches for the clinician's consideration, but are not intended as definitive or rigorous descriptions of Lead placement technique. Lead placement decisions and technique should be determined by the clinician, based on the type and location of the pain being treated, and based on standard clinical practice. The general guidance provided below can be adapted to other upper and lower extremity peripheral nerves as needed.

As stated, one objective of peripheral nerve stimulation may be to achieve pain relief through paresthesia sensation and/or comfortable muscle contraction in the target painful area. Test stimulation delivered via needle electrodes can assist in identifying the optimal lead location. Muscle response to electrical stimulation, and the patient's report of stimulus-evoked sensations (paresthesias) can provide guidance during test stimulation and lead placement. Also, Lead placement may be guided by ultrasound or fluoroscopy.

When identifying the percutaneous insertion site for the lead 400, it is preferable to consider where the patch assembly 100 will be worn in relation to the lead exit site. It is preferable that the patch assembly 100 be placed in a location such that there is minimal to no tension on the lead. Also, it is recommended that the patch be placed in a location that will be comfortable and easily accessible for the patient. As necessary, the lead insertion site should be adjusted to meet these criteria for optimal location of the patch.

Other considerations when placing the lead 400 and determining the location for the lead exit location may be one or more of the following: susceptibility to motion from postural changes, susceptibility to pressure from body weight, clothing, or position, and cleanliness and ease of access to clean.

As an example, the target nerve may be the peripheral branches of the axillary nerve located in the deltoid muscle. Needle electrodes may be used to locate the motor point(s) of the deltoid muscle using standard locations for clinical electromyography. For example, it may be desirable to contract both the middle and posterior heads of the deltoid muscle, and thus, two needle electrodes would be used to identify the middle and posterior deltoid motor points. The motor point of the middle deltoid is identified at the midpoint between the humeral tubercle and the deltoid tuberosity. With the shoulder fully adducted and in neutral rotation, this location corresponds to approximately 3-4 cm distal to the most anterior portion of the acromion. The motor point of the posterior deltoid is identified approximately 3-4 cm posterior to the motor point of the middle deltoid. Once these motor points are located (as evidenced by strong but comfortable muscle contractions and/or comfortable paresthesia sensation evoked during test stimulation), test stimulation may be delivered between the motor points using a third needle electrode to evoke contractions in both heads simultaneously. If necessary, the needle electrode can be repositioned toward the muscle with the weaker response until both heads contract strongly. The lead 400 should be placed in a preferred location, as described above. In this location, the patch assembly 100 may be placed on the insertion of the deltoid muscle at the deltoid tubercle (see FIG. 20) or in an alternative location.

FIGS. 21-26 show representative embodiments of the steps that representative instructions for use can incorporate or direct for the percutaneous placement of an intramuscular (IM) lead 400 for the activation of a muscle A and muscle B (e.g., the posterior and middle (lateral) deltoid muscles, respectively) in a system for the relief of pain, such as shoulder pain. The instructions may include a series of steps that can be followed to carry out portion or portions of the procedure. It is to be appreciated that these series of steps may be revised to place only one, or more than one IM lead(s) to activate one motor point in one muscle, or to activate two or more motor points in two or more muscles.

In an exemplary embodiment, the steps may include, but are not limited to:

1) Clean and prepare the skin surface area above the muscle(s) in which the IM lead will be placed. For example, the lateral aspect of the affected shoulder may first be cleaned with Betadine, and a local subcutaneous anesthetic (e.g., 2% lidocaine) may be administered.

2) Locate the motor points of two adjacent muscles (A and B) and mark them, e.g., with an indelible marker. For example, the motor points of the middle and posterior heads of the deltoid muscle may be located using the standard locations for clinical electromyography.

3) Place a needle electrode (e.g., 24 gauge EMG needle electrode) at the identified motor point locations for muscle A and B. For example, one needle electrode 20 is inserted through the skin towards motor point A and another needle electrode 22 is inserted through the skin towards motor point B (see FIG. 22). It is preferred that the each needle electrode 20,22 is inserted at least substantially perpendicular to a tangent of the skin surface at the respective insertion point.

4) Place a surface stimulation return electrode 24 (e.g. patch 100) in proximity of the area where needle electrode 20 and 22 have been placed, which may also be in proximity of the area in which the percutaneous lead 400 will be placed. Test stimulation may be applied to each needle electrode 20,22, inserted in muscle A and muscle B respectively, with the surface electrode 24 providing a return path for the test stimulation. The surface electrode 24 may be placed adjacent to the needle electrodes 20,22. Its position is not critical to the therapy and it can be moved throughout the therapy to reduce the risk of skin irritation.

Figure 23:
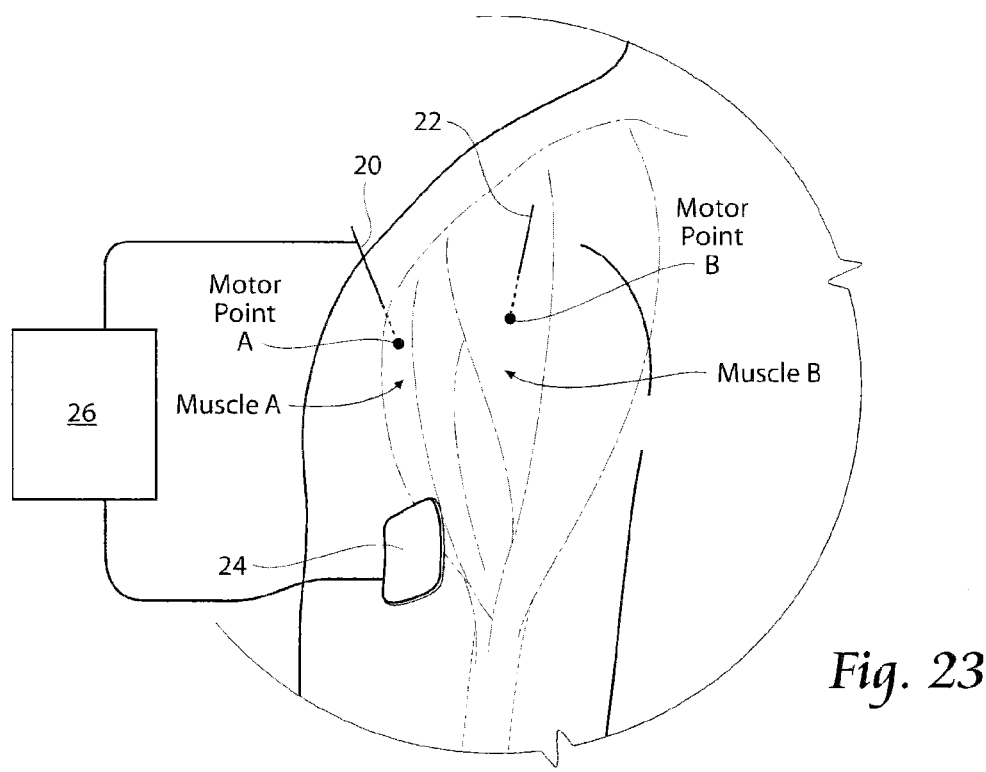
FIG. 23 is an anatomical view of the shoulder as shown in FIG. 22, showing a pulse generator coupled to one needle electrode and to the return electrode so that test stimulation may be delivered to stimulate the desired motor point.
Figure 24:
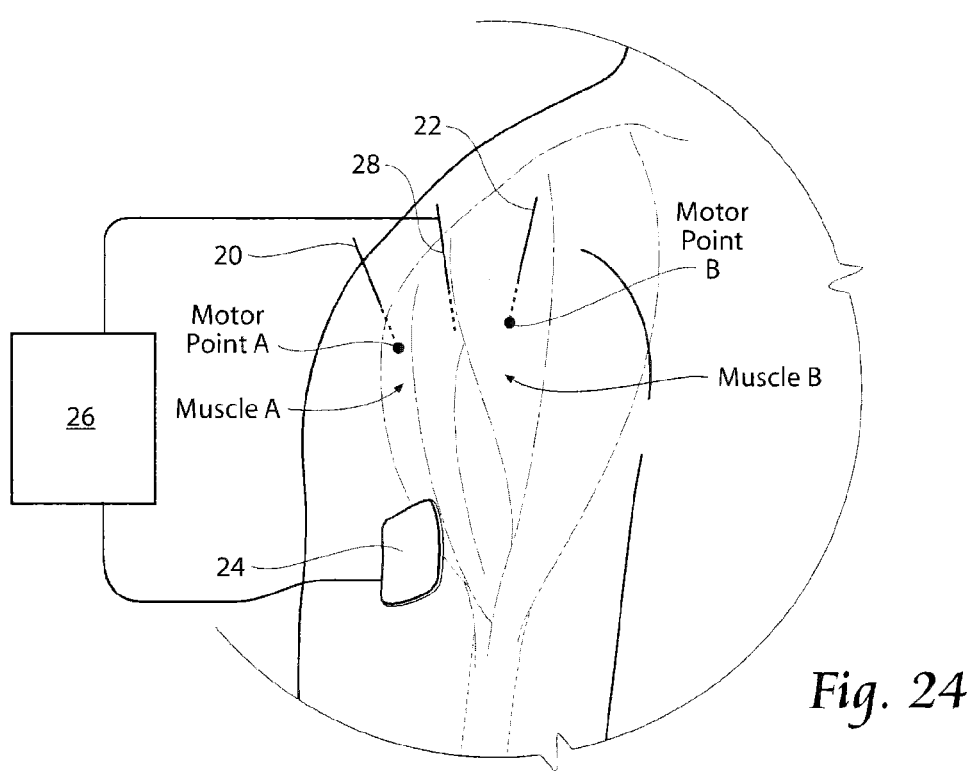
FIG. 24 is an anatomical view of the shoulder as shown in FIG. 22, showing the location at which both muscle A and muscle B can be activated simultaneously using one electrode, by placing a needle electrode at the approximate midpoint between the prior identified locations of needle electrodes for muscle A and muscle B respectively.
Figure 25:
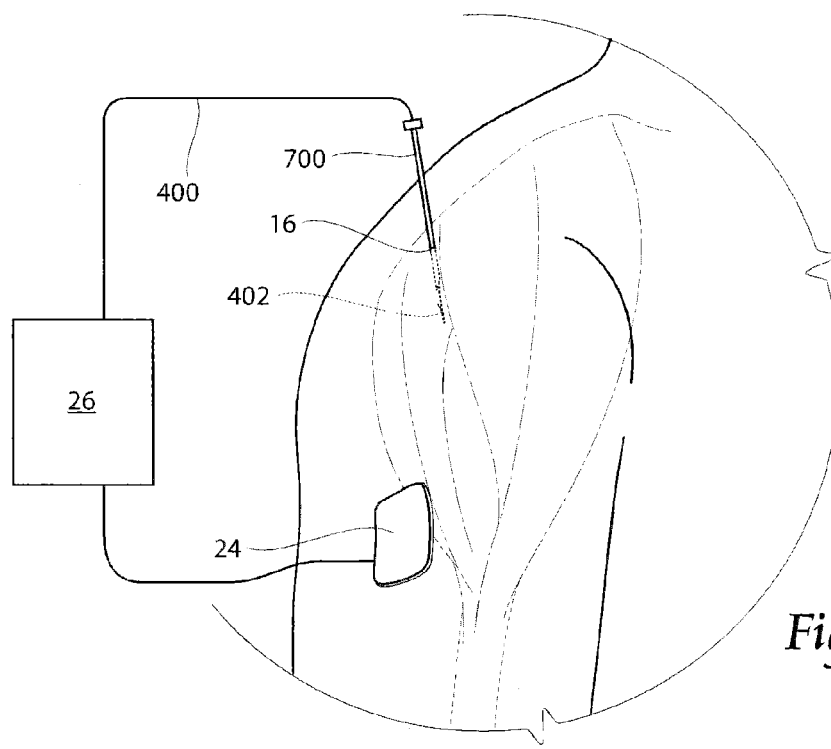
FIG. 25 is an anatomical view of the shoulder as shown in FIG. 22, showing the intramuscular lead and electrode placed percutaneously in the shoulder via an introducer needle.
Figure 26:
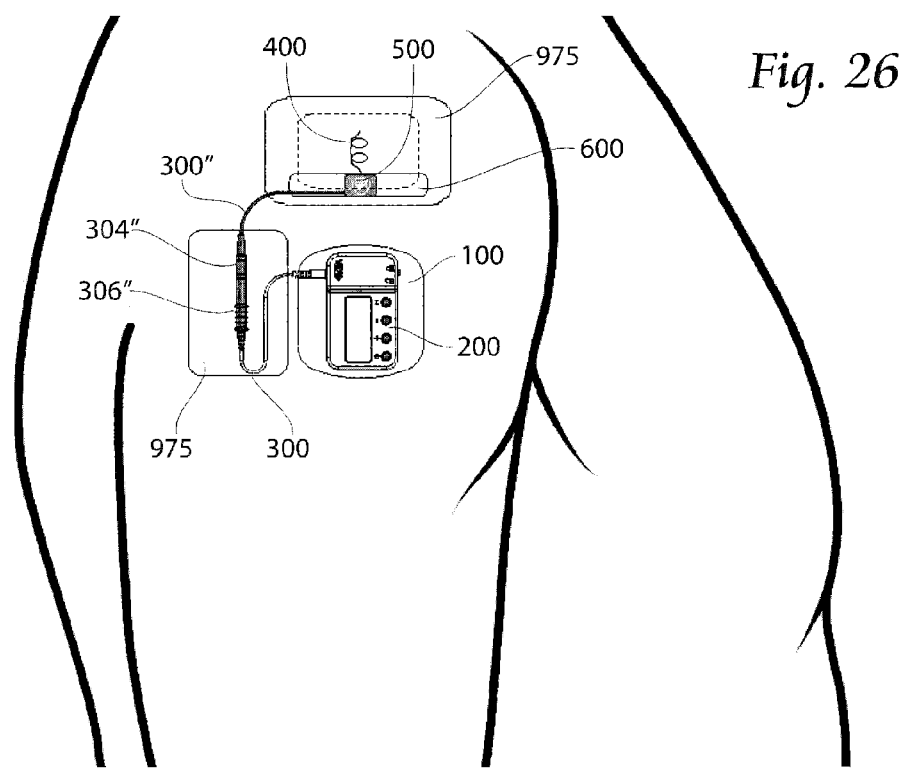
FIG. 26 is an elevation view of a system according to the present invention mounted on a user patient's arm.

5) Electrically couple a pulse generator 26 to a needle electrode 20 or 22 and to the return electrode 24 (see FIG. 23). Set the desired stimulation parameters for test stimulation to be delivered by the pulse generator 26. Test stimulation may be delivered using a current-regulated pulse generator, for example.

6) Deliver test stimulation to each needle electrode individually (i.e., one at a time) by slowly increasing the stimulation intensity. Stimulation intensity is defined here as the product of stimulation amplitude and stimulation pulse duration. Increasing the stimulation intensity can be achieved by keeping stimulation amplitude constant and increasing stimulation pulse duration, by keeping stimulation pulse duration constant and increasing stimulation amplitude, or by increasing both stimulation amplitude and stimulation pulse duration. For example, the stimulation intensity may initially be set at a very small, sub-sensation and sub-motor threshold level. Then, the stimulation intensity may be increased in small increments (e.g. 10 µs) to determine thresholds, for each motor point, at which the first sensation of stimulation occurs ($T_{SEN}$), at which stimulation evokes the first visible muscle contraction (motor threshold, $T_{MUS}$), and at which stimulation evokes the maximum tolerable muscle contraction ($T_{MAX}$).

7) Each needle location may need to be adjusted to a location that provides the strongest muscle contraction at the lowest stimulation intensity for each muscle. If the thresholds measured are determined to be high, it may be an indicator that the electrode is placed too far away from the motor point. Placing the electrode closer to the motor point, but not touching the motor point, may reduce one or more thresholds, and the motor point may be found when the threshold measurements are at a desired minimum. For example, if $T_{MUS}$ is close to $T_{MAX}$, the needle electrode may be repositioned to lower the threshold such that $T_{MUS} \ll T_{MAX}$, thus allowing for a strong contraction below the maximum tolerable stimulus intensity.

8) Record the stimulation intensity at which the first sensation occurs, at which the first noticeable muscle contraction occurs, and/or maximum tolerable muscle contraction occurs, for both muscle A and muscle B.

9) Determine the location at which both muscle A and muscle B can be activated simultaneously using one electrode. This determination may be made by placing a third needle electrode 28 at the approximate midpoint between the above identified locations of needle electrodes 20,22 for the motor points of muscle A and muscle B respectively (see FIG. 24). Alternatively 10) Deliver stimulation to the needle electrode 28 in an attempt to activate both muscle A and muscle B with the one electrode 28. For example, deliver stimulation, increasing stimulation intensity until both the middle and posterior deltoids muscles (i.e., muscle A and muscle B) are activated and are producing strong, visible, and palpable muscle contraction at a tolerable stimulus intensity.

11) If unable to achieve strong contraction of both muscles A and B at a tolerable stimulus intensity, remove the electrode 28 and translate it across the skin surface for a predetermined distance (e.g., approximately 0.5 cm) closer to the muscle that showed weaker contraction during stimulation applied in step 10, above.

12) Repeat stimulation delivery and placement location correction until both muscle A and muscle B contract at the desired level at a tolerable stimulus intensity.

13) Mark, note, and/or record this location with an indelible marker.

14) Record at which stimulation intensity first sensation, first noticeable muscle contraction, and maximum tolerable muscle contraction occurs by stimulation applied through the third needle electrode 28.

At this point in the process, three parameters, $T_{sen}$, $T_{mus}$, and $T_{max}$ have been measured for the three locations, i.e., motor point of muscle A, motor point of muscle B, and the location between motor point of muscle A and B to activate both muscles. The three parameters may be higher for the location in the middle due to its larger relative distance to the motor points at location A and B compared to both individual locations A and B.

For the described one lead approach, the parameters at location A and B may be used for guiding the exploration of finding the ideal location between A and B and the expected parameter range for the middle location. The parameters at the middle location are then used to program the parameters for stimulation to be applied through the IM lead to be placed in the middle depending on the desired application. An application might require sub-sensation stimulation, an application might require sub-motor (but supra-sensation) stimulation, an application might require supra-motor threshold stimulation, and yet another application might require stimulation at the maximum tolerable level. For example, the pain relief application described may require stimulation at $T_{max}$ in the middle location to activate the posterior and middle deltoid fully at the maximum tolerable stimulation intensity.

15) Remove all three needle electrodes 20, 22, and 28.

16) Identify the anticipated pathway of the percutaneous lead 400. The entry point of the lead may be a predetermined distance (e.g., approximately 2 to 3 cm) above the site identified as the location for the placement between the muscles A and B, such that the lead enters at an acute angle (e.g. less than 45 degrees) relative to a tangent of the skin surface, for example. This placement may aid in lead stability.

17) Administer a local anesthetic (e.g., 2% lidocaine) at the skin surface and along the anticipated pathway of the lead 400.

18) Insert the percutaneous lead 400 and electrode 402. For example, the lead may be placed percutaneously in the muscle via an introducer needle 700 (see FIG. 25), such as an insulated 20 gauge introducer needle.

19) Once the electrode 402 of the lead 400 has reached the desired location (i.e., at or near the final position of needle electrode 28), couple pulse generator 26 to the lead 400 and to the return electrode 24, and deliver stimulation to the lead 400 to verify proper placement. Both muscle A and muscle B desirably contract. Desirably, a strong, visible, and palpable contraction is evoked at a stimulus intensity that is tolerable for the participant.

Although not required, the position of the IM lead 400 or electrode 402 may be checked by imaging techniques, such as ultrasound or X-rays (fluoroscopy). Following placement of the lead(s), the portion of the leads which exits the skin may be secured to the skin using covering bandages and/or adhesives.

20) The stimulation intensity associated with first sensation of stimulation (i.e., $T_{SEN}$), first noticeable muscle contraction (i.e., $T_{MUS}$), and maximum tolerable contraction (i.e., $T_{MAX}$), may again be recorded.

It is preferred that the length of time to identify the optimal placement and place the IM lead to be less than one hour.

Terminating the Lead

Preferably after the lead 400 is situated at a desired position through the skin of a patient, the lead 400 is preferably terminated in a connector, such as the insulation displacement connector 500 previously described, which may already have a cable 300" installed thereon. The connector 500 may be provided with an indicator, such as an arrow, to guide lead insertion. The lead 400 may be drawn through the connector 500 until a desired length of the lead 400 is remaining between the connector 500 and the percutaneous exit site. Enough length should remain to allow for coiling of the lead for strain relief and so that the connector may be placed adjacent to the exit site and preferably under the same cover bandage 975. It is preferred to refrain from placing the connector 500 or any part of the connector mounting structure 600 immediately on top of the lead exit site.

Test stimulation may be provided through the cable 300" and connector 500 to ensure that there is an electrical connection between the electrode 402 and the cable 300" through the connector 500. Excess proximal length of the lead 400 may be trimmed. Preferably after the lead 400 has been secured in the connector 500, the connector mounting structure 600 is used, as described above, to secure the connector 500 to the skin near the exit site of the lead 400. The connector 500 should be placed on the connector mounting pad 602 such that the lead 400 exits preferably perpendicular to the longitudinal direction of the pad carrier 604. Excess lead length extending between the connector 500 and the lead exit site may be coiled to rest against the skin, such as by being placed under a waterproof bandage 975, which preferably covers both the lead exit site and connector 500, and more preferably the entire connector mounting structure 600.

User Interfaces and Usage

As described, the liquid crystal display (LCD) 220 and push buttons 222 allow therapy parameters to be set and compliance to be monitored, allow the user patient to turn stimulation on and off, and allow the user patient to make changes to the stimulus intensity within a predetermined stimulation range, preferably controlled and programmed by a clinician.

Button 222a may be referred to as a Mode button. The Mode button 222a preferably provides a menu navigation function. Further, the Mode button 222a may be preferably pressed and held for a predetermined time, such as four seconds, while the stimulator 200 is in one software mode, such as Clinician Mode, to cause the stimulator 200 to enter a second software mode, such as User Mode. The Mode button 222a may also be used to enter a software mode, such as Clinician Mode.

Button 222b may be referred to as a Decrease button. The Decrease button 222b may be pressed decrease a treatment parameter currently displayed on the screen 220 or to scroll down through multi-screen displays, such as logged error codes.

Button 222c may be referred to as an Increase button. The Increase button 222c may be pressed to increase a treatment parameter currently displayed on the screen 220 or to scroll up through multi-screen displays, such as logged error codes.

Button 222d may be referred to as a Start/Stop button. The Start/Stop button 222d may be pressed to turn the stimulator 200 on in a predetermined software mode, such as User Mode. The Start/Stop button 222d may also be used to turn stimulation therapy on and off. Further, the Start/Stop button 222d may be preferably pressed and held for a predetermined time, such as four seconds, to turn the stimulator 200 off to a standby state.

The slide switch 224 may be referred to as a Lock switch. The Lock switch 224 may be used to disable the stimulator buttons 222 to prevent accidental button activations. The switch 224 may be moved to a first, locked position to disable the buttons 222, and to a second, unlocked position, to enable the buttons 222. A lock icon preferably appears on the screen 220 to indicate when the switch 224 is in the locked position and the buttons 222 are locked.

Generally, there are preferably two modes of stimulator operation, User Mode and Clinician Mode. User Mode is the operation mode that user patients preferably use at all times. In User Mode, patients preferably are able to turn stimulation on and off, view time remaining in a therapy session, and make adjustments to the stimulus pulse duration within a predetermined range of parameters, preferably programmed by a clinician. Clinician mode is preferably used by clinicians to program-therapy parameters, view usage information and view any errors that may have been logged by the stimulator 200. Clinician Mode is preferably not accessible by patients. The stimulator 200 may be powered on in either User Mode or in Clinician Mode. To turn the stimulator 200 on in User Mode, the Start/Stop button 222d may be pressed and released. To turn the stimulator 200 on in Clinician Mode, it may be desirable to require a serial combination of buttons 222 to be pressed. For instance, while the stimulator 200 is turned off, a clinician may be required to press and hold the Mode button 222a while entering a serial combination of pressing and releasing two or more of the other buttons 222b,222c,222d. Such combination, or similar combination, aids to prevent patients from being able to change the detailed stimulation settings.

Once the stimulator 200 is on and in the Clinician Mode, the User Mode may be entered, such as by pressing and holding the Mode button 222a for a predetermined time, such as four seconds. The display 220 preferably displays a message, such as "USER" to indicate that User Mode has been entered. Additionally, it may be desirable to have an automatic transition from Clinician Mode to User Mode after a predetermined time of inactivity of the buttons 222, such as about five minutes. Such automatic transition may be desirable in the event that a clinician forgets to enter the User Mode, and perhaps sends a user patient on his or her way after an appointment. It is preferably that the Clinician Mode not be enterable from the User Mode if the stimulator 200 is on and in the User Mode. This is yet another safeguard to prevent user patient access to the Clinician Mode and alteration of detailed stimulation parameters.

In Clinician Mode, a clinician may program a range of pulse durations from which a user patient may select during home use. This gives the patient the flexibility to make minor adjustments to their treatment without the assistance of a clinician. Clinicians are able to program a minimum pulse duration, a "normal" pulse duration (pulse duration determined to be optimal), and a maximum pulse duration. The normal pulse duration is preferably equal to or greater than the minimum pulse duration. The maximum pulse duration is preferably equal to or greater than the normal pulse duration. If a pulse duration value is set out of an allowable range, the other two values preferably automatically adjust.

In User Mode, a patient may select from a predetermined number of stimulus intensities (pulse durations), such as the seven intensities shown in Table 1. The numbers −3 through +3 represent the relative intensities of the stimulus in a format that is easy for the patient to understand.

TABLE 1

Stimulus Intensities

| User Selectable Intensity | Programmed by Clinician |
| --- | --- |
| −3 | Minimum Pulse Duration |
| −2 | — |
| −1 | — |
| Norm | Normal Pulse Duration |
| +1 | — |
| +2 | — |
| +3 | Maximum Pulse Duration |

The pulse durations for settings −2, −1, +1, and +2 are preferably calculated such that the increments between −3, −2, −1, and Norm are equal, and the increments between Norm, +1, +2, and +3 are equal.

Programming the Stimulator

The stimulator may be preferably programmed with default values which may then be altered by a clinician. Preferred default values, ranges of allowable values, and increments of adjustment are given in Table 2. The default values may be restored to the stimulator by depressing a certain combination of buttons 222, such as by pressing and holding the Decrease button 222b and the Increase button 222c simultaneously for a predetermined amount of time, such as about four seconds, in the Clinician Mode of operation. A confirmatory message is preferably provided on the display 220, such as "DEF", to indicate restoration of default factory software conditions of the stimulator 200, including erasure of usage and error logs, may be restored to the stimulator by depressing a certain combination of buttons 222, such as by pressing and holding the Mode button 222a, the Decrease button 222b and the Increase button 222c simultaneously for a predetermined amount of time, such as about ten seconds, in the Clinician Mode of operation. A confirmatory message is preferably provided on the display 220, such as "FAC", to indicate restoration of factory default software conditions.

TABLE 2

Default values, ranges, and adjustment increments for treatment parameters.

| Parameter | Default | Minimum | Maximum | Adjusts in increments of |
| --- | --- | --- | --- | --- |
| Amplitude | 20 mA | 1 mA | 20 mA | 1 mA |
| Frequency | 12 Hz | 5 Hz | 25 Hz | 1 Hz |
| Pulse Duration Minimum | 20 μsec | 20 μsec | 200 μsec | 10 μsec |
| Pulse Duration Maximum | Pulse Duration Minimum | Pulse Duration Minimum | 200 μsec | 10 μsec |
| Pulse Duration Normal | Pulse Duration Minimum | Pulse Duration Minimum | Pulse Duration Maximum | 10 μsec |
| Therapy Time | 6 hours | 15 min | 12 hours | 15 min |
| Duty Cycle | 50% | 50% | 50% | N/A |

To program the stimulator 200, it may first be placed in the Clinician Mode of operation. The display 220 may provide a confirmatory indication, such as "OLIN" to indicate that the stimulator 200 is in the correct mode. A stimulus amplitude may then be displayed for adjustment, indicated, for example, by an "mA" on the display 220. The stimulus amplitude may be adjusted to a desired level by using the Decrease button 222b (to decrease the amplitude) or the Increase button 222c (to increase the amplitude). After the desired stimulus amplitude has been selected, the Mode button 222a may be pressed. A stimulus frequency may then be displayed for adjustment, indicated, for example, by an "Hz" on the display 220. The stimulus frequency may be adjusted to a desired level by using the Decrease button 222b (to decrease the frequency) or the Increase button 222c (to increase the frequency). After the desired stimulus frequency has been selected, the Mode button 222a may be pressed.

A stimulus minimum pulse duration may then be displayed for adjustment, indicated, for example, by an "μs" and "MIN" on the display 220. It is preferable to adjust the stimulation parameters while the stimulation is turned on, to confirm that the resulting stimulus is comfortable and results in a desired response. Stimulation may be turned on by pressing the Start/Stop button 222d. The minimum stimulation pulse duration may be adjusted to a desired level by using the Decrease button 222b (to decrease the pulse duration) or the Increase button 222c (to increase the pulse duration). If the minimum pulse duration is set to a value higher than the normal and/or maximum pulse duration, the value(s) for the normal and/or maximum pulse duration preferably automatically increase such that they match the minimum pulse duration, thus establishing a floor pulse duration level. It may be preferable to set the minimum pulse duration to the pulse duration at which first observable response (such as paresthesia or muscle twitch) occurs. After the desired minimum pulse duration has been selected, the Mode button 222a may be pressed.

A stimulus maximum pulse duration may then be displayed for adjustment, indicated, for example, by an "μs"

and "MAX" on the display 220. It is preferable to adjust the stimulation parameters while the stimulation is turned on, to confirm that the resulting stimulus is comfortable and results in a desired response. Stimulation may be turned on by pressing the Start/Stop button 222d. The maximum stimulation pulse duration may be adjusted to a desired level by using the Decrease button 222b (to decrease the pulse duration) or the Increase button 222c (to increase the pulse duration). If the maximum pulse duration is set to a value lower than the normal and/or minimum pulse duration, the value(s) for the normal and/or minimum pulse duration preferably automatically decrease such that they match the maximum pulse duration, thus establishing a ceiling pulse duration level. It may be preferred to set the maximum pulse duration to the pulse duration at which the maximum tolerable response occurs. After the desired maximum pulse duration has been selected, the Mode button 222a may be pressed.

A stimulus normal pulse duration may then be displayed for adjustment, indicated, for example, by an "µs" and "NORM" on the display 220. It is preferable to adjust the stimulation parameters while the stimulation is turned on, to confirm that the resulting stimulus is comfortable and results in a desired response. Stimulation may be turned on by pressing the Start/Stop button 222d. The normal stimulation pulse duration may be adjusted to a desired level by using the Decrease button 222b (to decrease the pulse duration) or the Increase button 222c (to increase the pulse duration). If the normal pulse duration is set to a value lower than the minimum pulse duration or higher than the maximum pulse duration, the value for the minimum or maximum pulse duration (the value that is out of range) preferably automatically changes such that t matches the normal pulse duration. It may be preferably to set the normal pulse duration to the pulse duration at which a strong response at a comfortable stimulus intensity occurs. After the desired normal pulse duration has been selected, the Mode button 222a may be pressed.

Upon entering a screen display in which pulse duration (minimum, normal, or maximum) is to be reviewed or adjusted, stimulation preferably automatically turns off to avoid sudden changes in pulse duration. Stimulation can be turned on by pressing and releasing the Start/Stop button 222d.

A stimulus therapy time, which is the time for which a stimulus regime may be delivered and after which stimulation is automatically discontinued, may then be displayed for adjustment, indicated, for example, by an "HRS" (an abbreviation for hours) on the display 220. The therapy time may be adjusted to a desired level by using the Decrease button 222b (to decrease the therapy time) or the Increase button 222c (to increase the therapy time). After the desired stimulus therapy time has been selected, the Mode button 222a may be pressed.

A usage time may then be displayed for review, indicated, for example, by an "HRS" and "USE" on the display 220. Preferably, the amount of stimulation time since the stimulator 200 was first activated is logged, including any test stimulation that has been delivered. After the usage time is reviewed, or to proceed to the next menu item, the Mode button 222a may be pressed.

Logged errors may then be displayed for review, indicated, for example, by a first number to the left of a colon and a second number to the right of a colon. The first number preferably indicates or provides an error code, while the second number preferably provides the number of times the error has been logged. The logged errors may be scrolled through by, for example, pressing the Decrease button 222b (to scroll up or down through the logged errors) or the Increase button 222c to scroll the opposite way. If further parameters are to be reviewed or adjusted, the Mode button 222a may be repeatedly pressed to cycle through the user output screens.

After programming is complete in the Clinician Mode, the stimulator 200 may be turned off by pressing and holding the Start/Stop button 222d, and then turned back on in User Mode by pressing and releasing the same button 222d, or otherwise placed in User Mode. Stimulation may be started by pressing and releasing the Start/Stop button 222d. Stimulation is preferably provided by the clinician to a user patient at each of the established programmed regimes to confirm that all intensities are comfortable for the patient. If necessary, Clinician Mode may be entered to make modifications to the stimulation parameters, or the regimes may be delivered to the patient while the stimulator 200 is in Clinician Mode prior to switching to User Mode.

A battery indicator is also preferably provided on the display 220. When the battery indicator provides indication of low battery, such as by a blinking indication, the power source for the stimulator 200 should be replaced, such as by replacing a patch assembly 100 if the power source is provided thereon, such as by the patch battery assembly 110.

System Use

Figure 21:
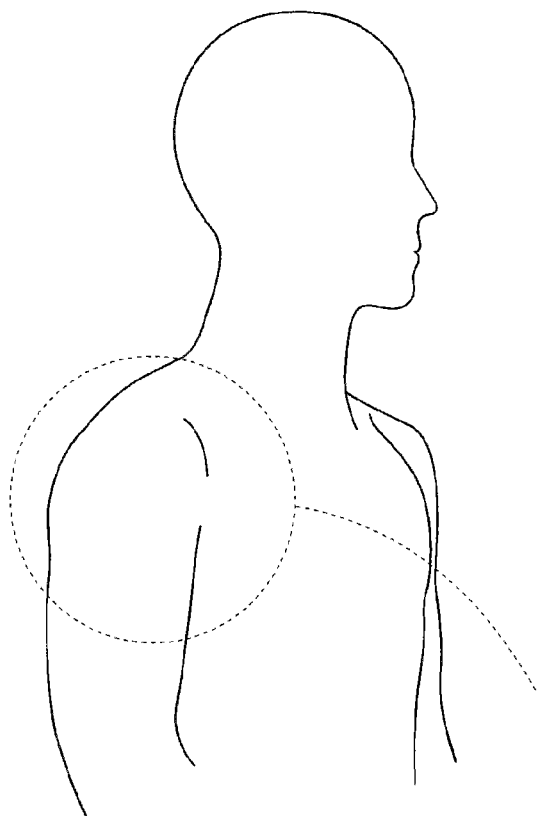
FIGS. 21 and 22 are anatomical views of a patient's shoulder showing the placement of a needle electrode placed in proximity to motor point A and a needle electrode placed in proximity to motor point B.
Figure 22:
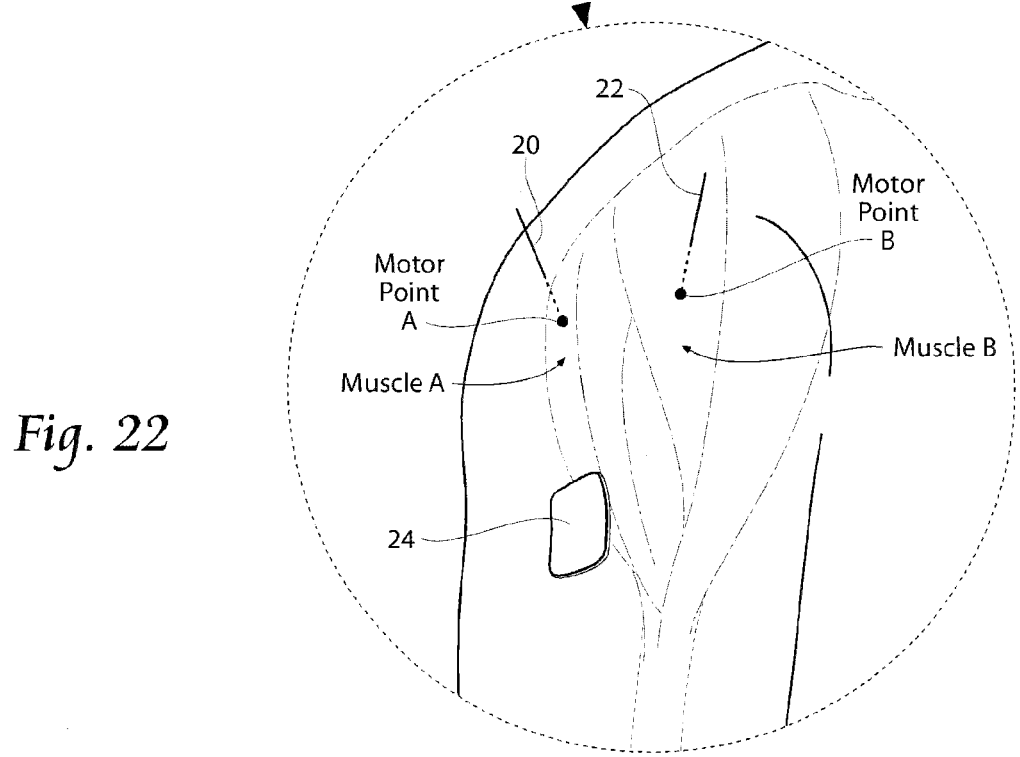

When it is desirable for a user patient to receive electrical stimulation, the stimulator 200 may be mounted to a patch assembly 100, and the patch assembly 100 may be mounted to the patient's skin. Optionally, for some patients, it may be desirable to apply a skin barrier product to the area where the patch assembly 100 will be adhered, to form a protective barrier on the skin. It is preferable to orient the stimulator 200 and patch assembly 100 such that there is minimal or no tension on the cable 300" and the lead 400 and it is easy for the person who will be operating the stimulator 200 to read the display 220. The first cable 300 may be used to couple the stimulator 200 to the electrode 402, to complete an electrical path through the lead 400, the connector 500, and the third cable 300". For instance the first connector element 302 may be mechanically and electrically coupled to the stimulator 200 and the second connector element 304 may be mechanically and electrically coupled to the first connector element 302" on the third cable 300". Optionally, the cables and/or connectors may be secured to the patient's skin using one or more waterproof bandages 975, as shown in FIGS. 20 and 21. Preferred bandages 975 to be applied to the lead exit site are preferably waterproof and primarily clear and may have a non-stick area in the middle such that the adhesive portion of the bandage 975 does not come in contact with the lead 400 (e.g., 3M Nexcare™ Waterproof Bandages, Knee and Elbow 582-10, 2⅜"×3½", or equivalent). If the adhesive portion of the bandage 975 comes in contact with the 400, there may be an increased risk of putting tension on the lead 400 when the bandage 975 is later removed. Applying tension on the lead 400 is undesirable as such forces can cause the electrode 402 to move from its intended location.

Stimulation may then be provided to and adjusted by the user patient. The adjustment can be accomplished by unlocking the switch 224 (if it was previously locked) and then using the Decrease button 222b or the Increase button 222c to adjust stimulation.

When stimulation is complete or it is otherwise desirable to remove components according to the present invention from a user patient, the stimulator 200 may be turned off, and the patch assembly 100 and cables may be disconnected and removed. The lead 400 may be trimmed to remove the connector 500, or the connector 500 may remain coupled to the lead 400 to aid in extraction. While applying steady tension to the exposed portion of the lead 400, the lead 400 may be gently pulled out of the patient's body. The lead 400 uncoils and the barb 414 straightens as the lead 400 is being pulled. It is preferred to inspect the lead 400 for signs of damage. If the lead 400 appears to be broken, the patient may be instructed to report any signs of pain, redness, swelling, discharge, or the appearance of a skin abscess. The lead exit site should be cleaned and bandaged as usual. It is possible that a fragment (or fragments) of the electrode 402 will break off and remain in the body after lead removal. If the lead 400 is being removed due to an infection, all fragments should be removed as well. In all other cases, clinical judgment may be used to determine whether or not the fragments should be removed. If fragments remain, the patient may be instructed to inspect the site and report signs of infection or granuloma. Should signs of infection appear, the fragments should be removed via an outpatient procedure. Any abscess may be lanced and the fragment(s) should be removed. A topical antibiotic may then be applied.

Placebo Mode of Operation

Additionally or alternatively, a sham or placebo mode of operation may be provided in the stimulator 200, preferably through software function switching. A sham mode of operation may be useful in conducting a placebo study or a double blind stimulation study. In sham mode, virtually all aspects of the stimulator operation are preferably substantially similar or identical to that of normal (non-sham) mode, especially in presentation to a user patient and/or clinician. For example:
  The user may be presented with an indication by the stimulator 200, such as an identifier on the display 220, that stimulus is being delivered.
  There are preferably no hardware, device, cable/lead, or labeling differences on the stimulator 200.
  Device implantation, setup and control are preferably identical to operation in non-sham mode.
  The treatment (albeit sham) time is, or time of purported stimulation, is preferably logged and may be displayed as if actual stimulation were being delivered.
  The battery indicator is preferably modified to appear as if the battery were draining similarly to normal use.

Sham mode may be entered through a software configuration, which may not be obvious to the user patient and/or clinician. For instance, sham mode may be entered by pressing a plurality of buttons 222 simultaneously for a predetermined amount of time, or by serially pressing and releasing a sequence of buttons 222, and may require that the stimulator 200 appear to be turned-off while such sequence is entered. The stimulator 200 may provide an indication of sham mode, such as by displaying an indication of a software mode that ends in the numeral 5, whereas a software version for normal mode of operation may end in a numeral 0.

Case Example

The subject was a 57-year old man musician with medical history of hypertension, hyperlipidemia, and glaucoma who developed neck and left shoulder pain with radiation to his left arm as a result of a motor vehicle collision 20 months prior to enrollment. He underwent x-ray imaging studies of his cervical spine and left shoulder, both of which were without acute or degenerative abnormality. No evidence of radiculopathy or plexopathy was found on electromyographic study of his left arm. He experienced persistent left shoulder pain with resolution of other symptoms and underwent an ultrasound guided subacromial injection of kenalog and lidocaine 16.5 months before enrollment. During the injection, it was noted that he had mild tendinopathy of the midsubstance of the supraspinatus muscle by ultrasound examination. He experienced mild relief as a result of the injection but his left shoulder pain persisted and he was referred for physical therapy. He completed six visits of physical therapy and was discharged 12 months before enrollment in the study in connection with the present invention with a home exercise program having only intermittent and limited pain. Five months before enrollment in this study, his pain worsened without provocation in spite of continued home exercise program. Just prior to enrollment he was taking acetaminophen and acetylsalicylic acid for pain.

On pre-procedure examination the subject exhibited no shoulder tenderness. He had 5 out of 5 muscle strength (Medical Research Council Scale) in internal rotation, external rotation, and abduction. He experienced a 8 out of 10 pain (0 being no pain, 10 pain worst imaginable) with Neer's sign that reduced to 0 of 10 with subacromial injection of 5 cc of 2% lidocaine. He did not have any evidence of overlying skin infection of the affected shoulder. He was not using opiate medications for pain relief. He was not receiving outpatient therapies for shoulder pain. He did not have any confounding conditions such as ipsilateral upper limb lower motor neuron lesion, Parkinson's disease, spinal cord injury, traumatic brain injury, multiple sclerosis, or complex regional pain syndrome. Baseline pain, pain interference, shoulder disability, and range of motion (ROM) are shown in Table 3.

TABLE 3

Baseline, during treatment, and post-treatment outcome measures.

|  | Baseline | Start of Stim | week 1 | week 2 | week 3 | 1 week post | 4 weeks post | 12 weeks post |
|---|---|---|---|---|---|---|---|---|
| BPI-3 | 8 | 7 | 6 | 3 | 2 | 1 | 0 | 0 |
| BPI-9 | 5.7 | 5.4 | 4 | 0.7 | 0 | 0.7 | 0 | 0 |
| DASH | 34.2 |  |  |  | 0.8 | 1.7 | 0 | 0.8 |
| Shoulder Flexion (degrees) | 129 |  |  |  | 155 | 170 | 165 | 180 |
| Shoulder Abduction (degrees) | 108 |  |  |  | 173 | 170 | 180 | 180 |

TABLE 3-continued

Baseline, during treatment, and post-treatment outcome measures.

|  | Baseline | Start of Stim | week 1 | week 2 | week 3 | 1 week post | 4 weeks post | 12 weeks post |
|---|---|---|---|---|---|---|---|---|
| Shoulder Ext Rotation (degrees) | 76 |  |  |  | 75 | 80 | 83 | 79 |
| PPT Affected Deltoid (kg/cm$^2$) | 5.6 | 9.0 |  |  | 8.1 | 9.3 | 5.9 | 5.9 |
| PPT Contralateral Deltoid (kg/cm$^2$) | 5.7 | 7.4 |  |  | 9.3 | 6.2 | 6.4 | 6.9 |
| PPT Contralateral Tibialis Anterior (kg/cm$^2$) | 6.4 | 6.1 |  |  | 8.2 | 8.8 | 4.5 | 8.4 |

BPI-3: Worst pain in the last week, 0 (None)-10 (Worst imaginable)
BPI-9: Average of the scores for the seven domains on a 0 (no interference)-10 (complete interference) with general activity, mood, walking ability, normal work, relations with other people, sleep, and enjoyment of life during the last week
DASH: a measure of physical function and symptoms in people with musculoskeletal disorders of the upper limb ranging from 0 (no disability) to 100 (complete disability
Shoulder Flexion: Measured by handheld goniometer with patient standing
Shoulder Abduction: Measured by handheld goniometer with patient standing
Shoulder External Rotation: Measured by handheld goniometer with lying supine, starting position of hand on abdomen
PPT: Pressure-Pain Thresholds - The amount of pressure (kg/cm$^2$) from a handheld algometer where a sensation of pressure first changes to pain. The average of 3 measurements at each location is reported.

The formal 4-month intervention protocol included electrode implantation, 1-wk of electrode stabilization, 3-wks of PNS treatment, and 3-months of follow-up. The primary outcome was the Brief Pain Inventory Short-form Question 3 (BPI 3), which rates the "worst pain" in the prior week on a 0-10 numeric rating scale, where 0 indicates "no pain" and 10 indicates "pain as bad as you can imagine." Secondary outcomes were: 1) Brief Pain Inventory Short-form Question 9 (BPI 9), a measure of pain interference with daily activities, including general activity, mood, walking ability, normal work, relations with other people, sleep, and enjoyment of life during the last week on a 0-10 numeric rating scale, where 0 indicates "does not interfere" and 10 indicates "completely interferes." The BPI 9 score is the average of the scores for the seven domains; 2) the Disabilities of Shoulder, Arm, and Hand (DASH) questionnaire, a measure of physical function and symptoms in people with musculoskeletal disorders of the upper limb ranging from 0 (no disability) to 100 (complete disability); 3 the Patient Global Impression of Change (PGIC), a 6-point subjective measure of change in activity limitations, symptoms, emotions, and quality of life due to symptoms since the beginning of treatment; 4) pain-free range of motion of the glenohumeral joint (internal rotation, external rotation, and abduction); and, 5) Pressure-pain threshold measurement (PPT) of the deltoid of the affected shoulder, contralateral shoulder, and contralateral tibialis anterior. The PPT is a measure of deep somatic tissue sensitivity, indicated by the amount of pressure (kg/cm2) from a handheld algometer where a sensation of pressure first changes to pain. The average of 3 measurements at each location is reported.

The skin overlying the deltoid muscle was cleaned with povidone-iodine topical antiseptic. Monopolar needle electrodes were inserted perpendicular to the skin surface at the motor points of middle and posterior deltoids. Motor points were confirmed by stimulating each muscle separately and demonstrating strong contraction of the middle and posterior deltoids. A third needle electrode was placed at a midpoint between the two motor points. The position and depth of the electrode and the pulse duration were iteratively adjusted until strong contraction of both heads was achieved.

A 20-gauge insulated introducer loaded with a percutaneous lead was then inserted perpendicular to a tangent of the skin surface to the depth and location indicated by the third needle electrode. The characteristics of the percutaneous lead have been previously described. The electrode was supplied with stimulation to verify proper position. Pressure was maintained at the skin surface to anchor the electrode's barb in the belly of the muscle and the introducer was withdrawn leaving the electrode in place. Stimulation was delivered to the electrode again to ensure proper placement. A dry sterile dressing was placed over the electrode and an occlusive dressing was applied. Prior to leaving the clinic, the subject was instructed on the proper care of the lead exit site. He returned 48-hours later for examination of the skin.

Following a one week stabilization period, the stimulator was connected to the lead and parameters were set to stimulate the middle and posterior deltoids at 12 Hz and 20 mA with a pulse duration of 60 µs. The stimulation provided strong contraction of both deltoids. The subject was prescribed 6-hrs of stimulation per day. The stimulator completed a cycle every 30 seconds consisting of 5 seconds ramp up, 10 seconds maximum stimulation, 5 seconds ramp down, and 10 seconds relaxation. During the 3-wk stimulation phase he was contacted by telephone weekly and queried for pain intensity, adverse events, and medication usage.

At the end of the 3-wk stimulation phase the subject returned for evaluation of primary and secondary endpoints including BPI 3, BPI 9, the DASH, PGIC, pain free ROM, and PPT measurement. Medication usage and adverse events were also recorded. Compliance data were captured by the stimulator datalogger. The electrode was then removed by gently pulling on the exposed end of the lead. He underwent anterior-posterior and scapular-Y view radiographs of the shoulder for surveillance for retained electrode fragments. He returned at 1, 4, and 12-wks post-treatment for skin evaluation and outcomes assessments.

The subject tolerated the implantation and stimulation test procedure well. The 3-wk stimulation protocol was completed with adverse events of mild discomfort when flexing his shoulder simultaneously with receiving stimulation and a localized tissue inflammation granuloma at the site of the electrode that resolved by his 1-month follow-up. The subject reported 100% compliance with the protocol, although the stimulator recorded 94% compliance. The outcome measurements for different study time points are listed in Table 3. The subject experienced 75.0% and 100% reduction in pain (BPI 3) at end of treatment relative to baseline and at 3 months post-treatment, respectively. He used aspirin or acetaminophen rarely in the follow-up period, and denied use at his 3-month follow-up. There was improvement in pain related quality of life (BPI 9) to where he had no pain interference at the 1 and 3 month follow-up visits. His arm function improved with a 97.6% reduction in his DASH score. This was confirmed by the Patient Global Impression of Change Scale, which was rated "very much improved" from end of treatment through the 3-month follow-up. Pain-pressure thresholds measured at the affected deltoid, non-affected deltoid, and tibialis anterior were increased at all points after baseline.

This working example describes the first subject treated with a single-lead PNS system for SIS. After three weeks of electrical stimulation, he experienced substantial pain reduction that was maintained for at least three months after completion of treatment. The BPI 9, DASH, PGIC, pain free ROM, and PPT data suggest that the intervention might also reduce impairment, and improve function, and improve quality of life.

The mechanism of pain relief may have been the result of improvement in biomechanics of the subject's shoulder, as evidenced by improved ROM, though PNS resulting in pain relief in stroke survivors with chronic shoulder pain has been achieved with inconsistent improvements in biomechanics. Alternatively or additionally, stimulation of low-threshold myelinated primary afferents may decrease the response of the dorsal horn neurons to unmyelinated nociceptors. This is similar to the purported mechanism in which transcutaneous electrical nerve stimulation (TENS) reduces pain. However, the duration of pain relief this subject has experienced would not be expected with, nor has it been thought to be achievable by, treatment by TENS.

Additionally or alternatively, PNS delivered according to the present invention may reduce chronic pain by altering maladaptive neuroplasticity in the central nervous system that causes central hypersensitivity. There is evidence that chronic pain can be perpetuated by maladaptive neuroplastic changes within the central nervous system. Evidence of central hypersensitivity has been demonstrated by lower local and distal PPTs in those with chronic SIS compared to controls. This subject had improvements in local and distal PPTs, demonstrating that a central mechanism may be modulated through PNS. That is, in the chronic phase of SIS central sensitization, a form of maladaptive neuroplasticity, may have a dominant role in pain perception. While acute injury is often initiated and maintained by inflammatory processes, chronic injury likely reflects perturbations within the neural axis involving both spinal and supraspinal neural structures. This is likely the reason that treatments appropriate for the acute stage of SIS are no longer appropriate for those who experience chronic pain from SIS. Thus, reversal or bypass of maladaptive neural plasticity, because same is a pain mediator, is a target of this novel treatment.

Treatment of chronic pain with PNS may be understood with reference to updated conceptual framework of pain by Melzack, the neuromatrix theory of pain and the theory of central sensitization. The neuromatrix theory posits that pain is a multidimensional experience produced by neurosignature patterns within the neuronal network of the brain. These patterns can be produced by sensory inputs (as in nociceptive pain) or lack of sensory inputs (as in phantom limb pain). The actual experience of pain is produced by the output of a neuronal network rather than sensory input; however, sensory input can be altered by central sensitization. Central sensitization is an increase in the function of neurons and circuits in nociceptive pathways that can become a trigger for the painful neurosignature pattern. The pathways susceptible to central sensitization are widespread within the CNS and include locations from the dorsal horn to the prefrontal cortex. Failure of homeostatic mechanisms allow persistence of central sensitization or the pain provoking neurosignature pattern after the injury resolves, which creates a chronic hypersusceptibility to pain from normally innocuous movements.

Neuroplastic changes of the central nervous system associated with chronic pain have been shown to lead to hypersensitivity. The hypersensitivity is displayed as local and generalized lowered pain thresholds, exaggerated pain response to painful stimulation, enlargement of painful areas, and lower threshold for spinal reflexes. Evidence of this hypersensitivity in chronic SIS has been shown with reduction in pressure pain thresholds in local (primary hyperalgesia) and distant pain-free areas (secondary hyperalgesia) compared to controls without shoulder pain. The pressure-pain thresholds were correlated with pain severity symptoms (lower shoulder pain was associated with higher pain thresholds). Evidence of reduced pain thresholds associated with central nervous system changes has been found in subjects with chronic pain who displayed a lower spinal reflex threshold and lower pressure pain thresholds when compared to controls without chronic pain.

There is also evidence that the hypersensitivity is preceded by chronic pain. A longitudinal population study has shown that those who acquired chronic pain developed mechanical hypersensitivity, as measured by pressure pain thresholds, whereas stable thresholds were observed in those who did not develop chronic pain.

To alter this maladaptive neuroplastic change, and thus alter a pain experience, preferably by reducing pain, a shift in neural networks needs to occur (whether excitatory or inhibitory) causing a shift to a neurosignature pattern that does not confer the experience of pain. Therapeutic electrical stimulation delivered according to embodiments of the present invention activates dormant neuronal networks that, when activated, disrupt the pathophysiological neuronal networks and thereby diminish symptoms. Not only can electrical stimulation be used to control acutely activated networks, but previously dormant networks can become persistently activated by a repetitive electrical stimulation protocols. IM PNS mediated muscle contraction provides physiologic activation of muscle spindles and golgi tendon organs, which in turn provide patterned afferent input to the CNS This differentiates IM PNS from spinal cord stimulation, peripheral nerve field stimulation and TENS.

Thus, electrical stimulation mediated sensory modulation can be used to sustain functional reorganization of maladaptive neuroplastic changes of the nervous system that is associated with chronic pain.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:
1. A method comprising the steps of:
placing an electrode in subepidermal tissue of a human; and
delivering electrical stimulation through the electrode, wherein, after the delivering step, a level of pain perceived by the human, wherein the pain was caused by or occurring secondarily to subacromial impingement syndrome, is reduced.

2. A method according to claim 1, wherein during the delivering step, a level of pain perceived by the human, wherein the pain was caused by or occurring secondarily to subacromial impingement syndrome, is reduced.

3. A method comprising the steps of:
   percutaneously inserting or instructing percutaneous insertion of a lead into a patient, the lead having an electrode wherein the electrode is positionable in sub-epidermal tissue of the patient;
   delivering or instructing delivery of electrical stimulation through the electrode altering maladaptive neuroplasticity in a central nervous system of the patient; and
   reducing or eliminating chronic pain of the patient.

4. The method of claim 3, wherein the lead is attached with the electrode.

5. The method of claim 3, wherein the electrode is formed as part of the lead.

6. The method of claim 3, wherein the lead includes a portion having an insulated body and the electrode is formed from a portion of the lead free of the insulated body.

7. The method of claim 3 further comprising producing or instructing production of a muscle contraction in a target area.

8. A method comprising the steps of:
   percutaneously inserting or instructing percutaneous insertion of a lead into a patient;
   placing or instructing placement of an electrode in sub-epidermal tissue of the patient, the electrode operatively coupled with the lead;
   delivering or instructing delivery of electrical stimulation through the electrode to generate a muscle contraction in a target area;
   reducing or instructing reduction of central hypersensitivity in the patient; and
   producing or instructing production of a therapeutic effect of reducing chronic pain in the patient.

9. A method comprising the steps of:
   percutaneously inserting or instructing percutaneous insertion of a lead into a patient;
   placing or instructing placement of an electrode in sub-epidermal tissue of the patient, the electrode operatively coupled with the lead;
   delivering or instructing delivery of electrical stimulation through the electrode to generate a muscle contraction in a target area; and
   sustaining or instructing sustaining of functional reorganization of maladaptive neuroplastic changes of a nervous system of the patient associated with chronic pain.

10. A method comprising the steps of:
    percutaneously inserting or instructing percutaneous insertion of a lead into a tissue of a human; and
    delivering or instructing delivery of stimulation through at least one electrode operatively coupled with the lead to a neurological motor point of the human;
    generating or instructing generation of a muscle contraction in a target area; and
    changing or instructing change of central nervous system maladaptive neuroplasticity of the human producing a therapeutic effect to reduce chronic pain.

* * * * *